US009743827B2

United States Patent
Yasunaga et al.

(10) Patent No.: US 9,743,827 B2
(45) Date of Patent: Aug. 29, 2017

(54) ENDOSCOPE

(71) Applicant: OLYMPUS CORPORATION, Tokyo (JP)

(72) Inventors: Koji Yasunaga, Hino (JP); Yuta Sekiguchi, Hachioji (JP); Yuta Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/133,266

(22) Filed: Apr. 20, 2016

(65) Prior Publication Data

US 2016/0227986 A1 Aug. 11, 2016

Related U.S. Application Data

(63) Continuation of application No. PCT/JP2014/074222, filed on Sep. 12, 2014.

(30) Foreign Application Priority Data

Nov. 7, 2013 (JP) ................................. 2013-231106

(51) Int. Cl.
| | |
|---|---|
| *A61B 1/005* | (2006.01) |
| *G02B 23/24* | (2006.01) |
| *A61B 1/00* | (2006.01) |

(52) U.S. Cl.
CPC ........ *A61B 1/0057* (2013.01); *G02B 23/2476* (2013.01)

(58) Field of Classification Search
CPC ..... A61B 1/0057; A61B 1/005; A61B 1/0051; A61B 1/0052; A61B 1/00066; G02B 23/2476

(Continued)

(56) References Cited

U.S. PATENT DOCUMENTS

| | | | |
|---|---|---|---|
| 4,718,407 | A | 1/1988 | Chikama |
| 4,721,099 | A | 1/1988 | Chikama |

(Continued)

FOREIGN PATENT DOCUMENTS

| | | |
|---|---|---|
| EP | 2039284 A1 | 3/2009 |
| EP | 2671499 A1 | 12/2013 |

(Continued)

OTHER PUBLICATIONS

International Search Report dated Dec. 16, 2014 issued in PCT/JP2014/074222.

(Continued)

*Primary Examiner* — Timothy J Neal
(74) *Attorney, Agent, or Firm* — Scully, Scott, Murphy & Presser, P.C.

(57) ABSTRACT

An endoscope includes: operation wires insertedly arranged inside an insertion portion and an operation portion, the operation wires causing a bending portion to bend by being pulled/slackened; an operation member provided on the operation portion, the operation member performing a bending operation of the bending portion; a rotation member provided in the operation portion, the rotation member pulling/slackening the operation wires by rotating in conjunction with an operation of the operation member; and an amount-of-operation-force reducing portion giving rotation torque in a direction in which the rotation member inclines to reduce an amount of operation force of the operation member, in response to inclination of the operation member, wherein the rotation torque of the amount-of-operation-force reducing portion changes in conjunction with displacement of the operation member operated, and the amount-of-operation-force reducing portion offsets and reduces the amount of operation force required for the operation member.

10 Claims, 19 Drawing Sheets

(58) Field of Classification Search
USPC .................................... 600/145–150
See application file for complete search history.

(56) References Cited

U.S. PATENT DOCUMENTS

2009/0076330 A1* 3/2009 Ashida ................. A61B 1/0052
600/146
2013/0267775 A1 10/2013 Okamoto

FOREIGN PATENT DOCUMENTS

| | | |
|---|---|---|
| JP | S56-125202 U | 9/1981 |
| JP | S57-185828 A | 11/1982 |
| JP | S62-038411 A | 2/1987 |
| JP | S62-74801 U | 5/1987 |
| JP | S62-74803 U | 5/1987 |
| JP | S62-160903 U | 10/1987 |
| JP | 2008-035882 A | 2/2008 |
| JP | 2009-089955 A | 4/2009 |
| JP | 2009-090087 A | 4/2009 |
| JP | 2012-100683 A | 5/2012 |
| JP | 5330625 B1 | 10/2013 |
| WO | WO 2013/047186 A1 | 4/2013 |
| WO | 2015/156046 A1 | 10/2015 |

OTHER PUBLICATIONS

Japanese Office Action dated Aug. 18, 2015 issued in JP 2015-527390.
Extended Supplementary European Search Report dated Jun. 7, 2017 in European Patent Application No. 14 86 0905.0.

* cited by examiner

ENDOSCOPE

CROSS REFERENCE TO RELATED APPLICATION

This application is a continuation application of PCT/JP2014/074222 filed on Sep. 12, 2014 and claims benefit of Japanese Application No. 2013-231106 filed in Japan on Nov. 7, 2013, the entire contents of which are incorporated herein by this reference.

BACKGROUND OF INVENTION

1. Field of the Invention

The present invention relates to an endoscope which has a bending portion at a distal end side of an insertion portion and in which a bending operation of the bending portion is performed by a bending operation member provided on an operation portion on a hand side.

2. Description of the Related Art

Recently, endoscopes have been widely used in a medical field and an industrial field. In some endoscopes, an elongated insertion portion is flexible, and, generally, a bending portion which can be freely bending-operated in a predetermined direction according to a user's operation at hand is provided on a distal end side of the insertion portion.

In such an endoscope having the insertion portion which is provided with the bending portion, it is possible to, by causing the bending portion to bend, change an observation direction of an observation optical system provided at a distal end portion located on the more distal end side of the insertion portion than the bending portion so that examination for a wide range can be performed.

Conventional endoscopes are configured such that a bending operation of the bending portion is performed on a hand side by the operation member of a lever type, a joystick type or the like which is provided on the operation portion, for example, as disclosed in Japanese Patent Application Laid-Open Publication No. S62-38411 or Japanese Patent Application Laid-Open Publication No. 2009-89955.

SUMMARY OF THE INVENTION

An endoscope of an aspect in the present invention includes: an insertion portion provided with a bending portion at a distal end part; an operation portion coupled to the insertion portion; four operation wires insertedly arranged inside the insertion portion and the operation portion, the four operation wires causing the bending portion to bend by being pulled/slackened; one operation member provided on the operation portion, the operation member having a rotation portion and being capable of performing a bending operation of the bending portion in four directions by being inclined with the rotation portion as a center; a rotation member provided in the operation portion and having a proximal end side and a distal end side, the proximal end side being connected to an opposite side of the operation member with the rotation portion as a center, and the rotation member pulling/slackening the four operation wires by being inclined with the rotation portion as a center in conjunction with an inclination operation of the operation member; and an amount-of-operation-force reducing portion, an end portion of which is movably held on the distal end side of the rotation member, the amount-of-operation-force reducing portion giving rotation torque in a direction in which the rotation member is inclined, in response to inclination of the operation member, to reduce an amount of operation force of the operation member, wherein the rotation torque of the amount-of-operation-force reducing portion changes in conjunction with displacement of the operation member operated, and the amount-of-operation-force reducing portion offsets and reduces the amount of operation force required for the operation member.

According to the present invention described above, it is possible to provide an endoscope which reduces an amount of operation force of an operation member for performing a bending operation of a bending portion to prevent a user from being tired and make it possible to perform a slight bending operation.

DETAILED DESCRIPTION OF THE PREFERRED EMBODIMENT(S)

The present invention will be described below with use of drawings.

Note that attention should be paid to that, in description below, the drawings based on embodiments described below are schematic, and a relationship between thickness and width of each portion, a ratio among thicknesses of respective portions and the like are different from an actual relationship, ratio and the like, and that there may be a case where a portion having a different size relationship and ratio is included among the drawings.

First, an embodiment of an endoscope of an aspect of the present invention will be described below based on drawings. Note that, though description will be made below on a rigid endoscope in which an insertion portion is rigid, as an example, the technique is not limited to the rigid endoscope but is also applicable to a flexible endoscope in which the insertion portion is a flexible tube.

(First Embodiment)

First, a first embodiment of the present invention will be described.

Figure 1:
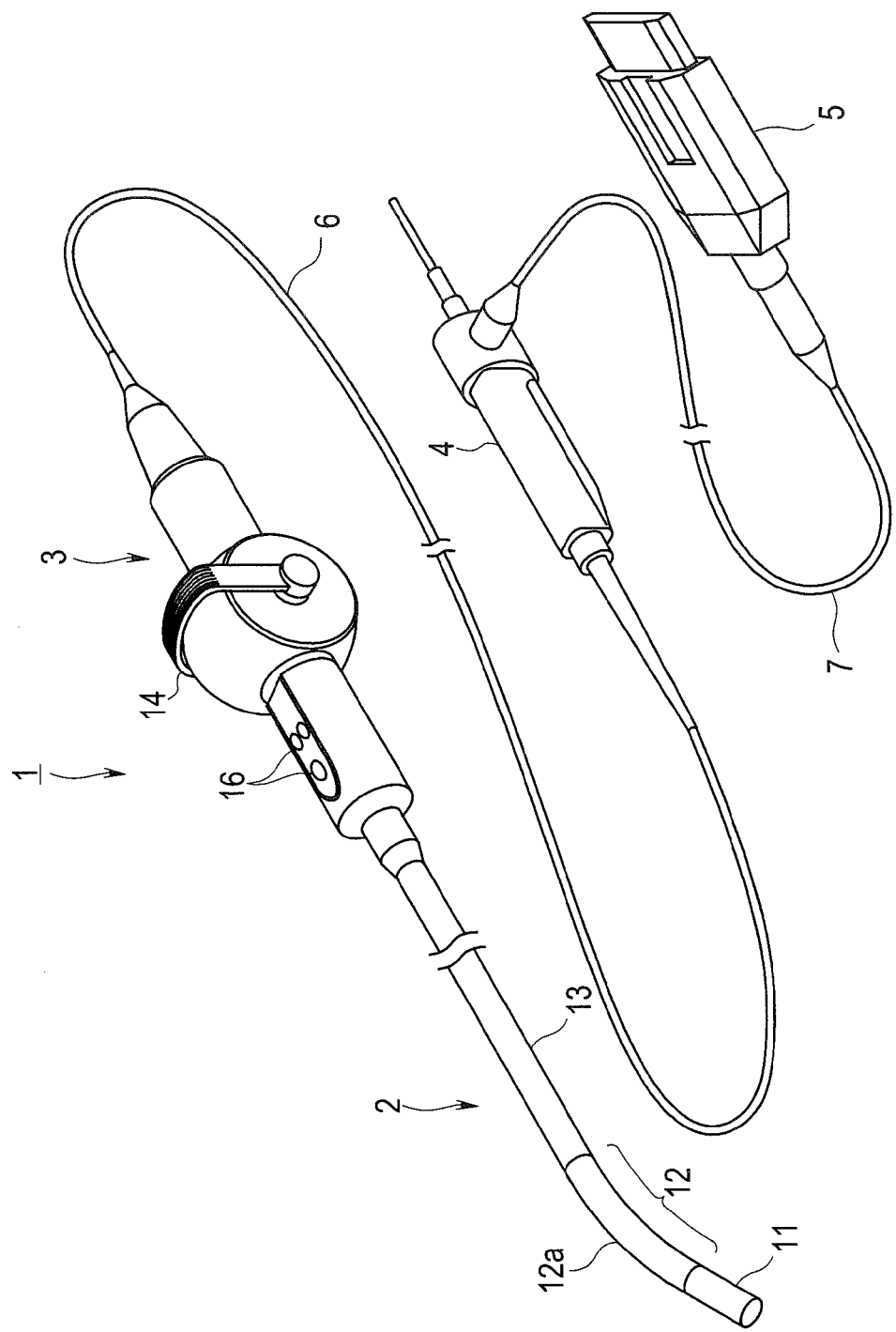
FIG. 1 is a perspective view showing a general configuration of an endoscope of an aspect according to a first embodiment of the present invention.
Figure 2:
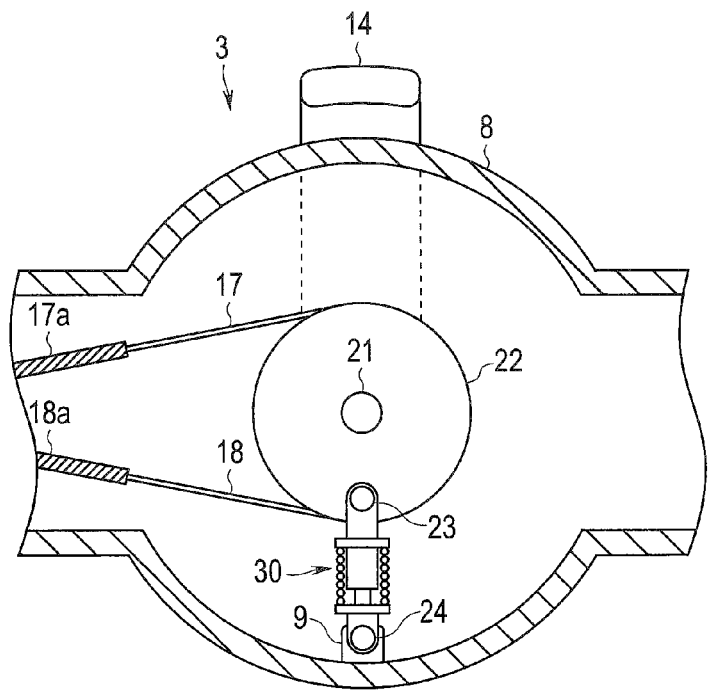
FIG. 2 is a cross-sectional view showing an internal configuration of an operation portion according to the first embodiment of the present invention.
Figure 3:
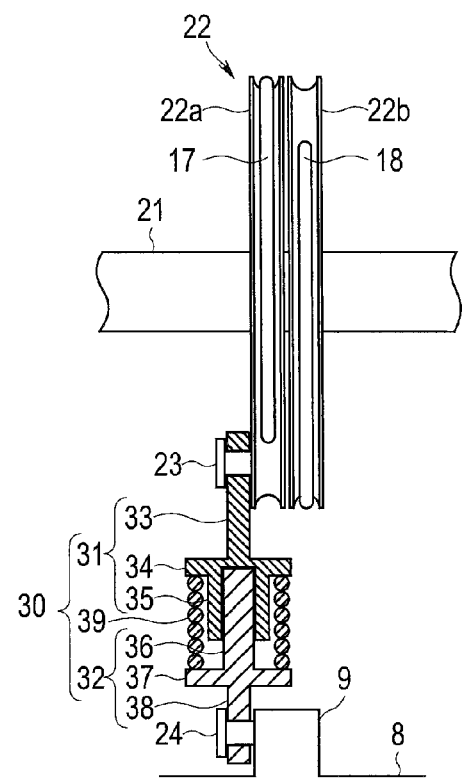
FIG. 3 is a partial cross-sectional view showing a configuration of a pulley unit and an amount-of-operation-force reducing portion which are provided in the operation portion according to the first embodiment of the present invention.
Figure 4:
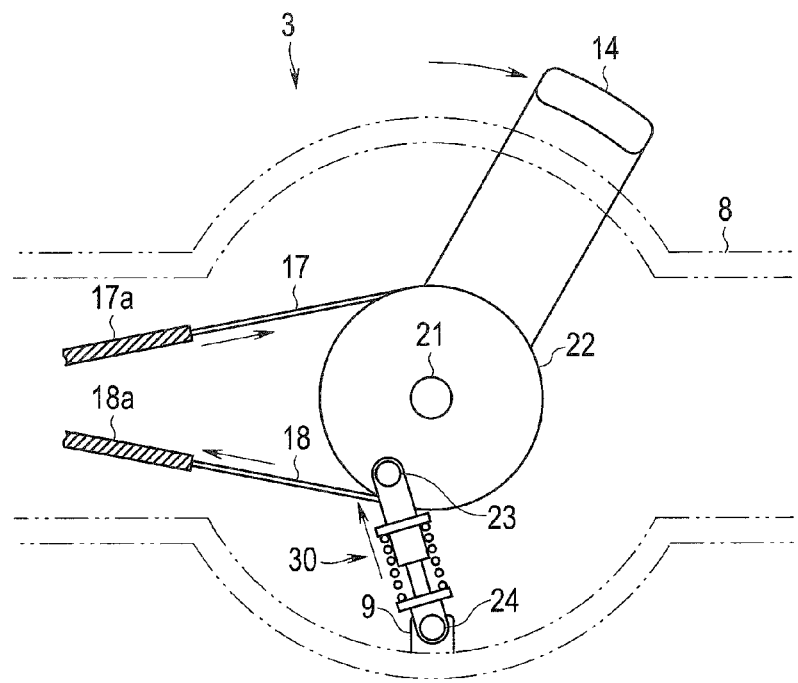
FIG. 4 is a diagram illustrating action of the amount-of-operation-force reducing portion in a state that a bending portion is bent to an upper part side according to the first embodiment of the present invention.
Figure 5:
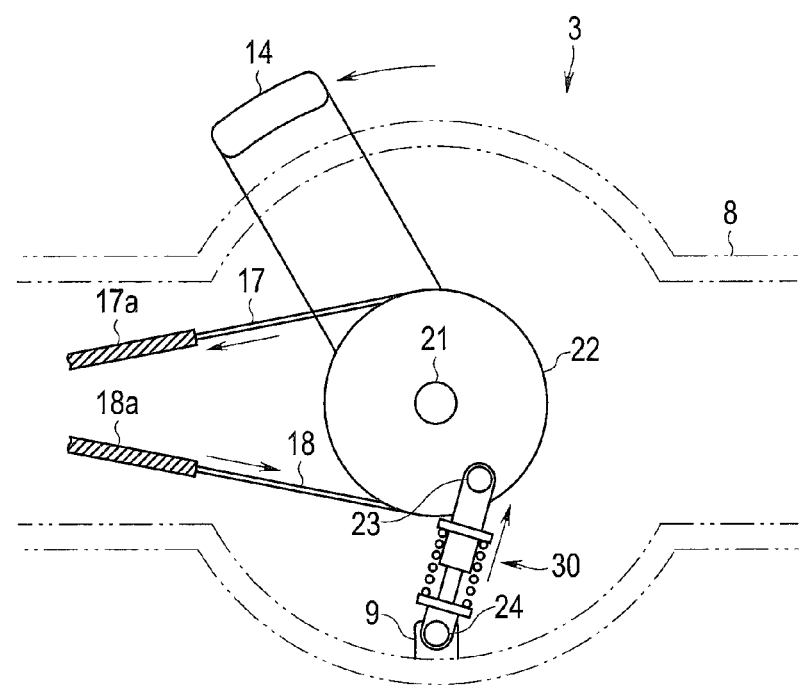
FIG. 5 is a diagram illustrating action of the amount-of-operation-force reducing portion in a state that the bending portion is bent to a lower part side according to the first embodiment of the present invention.
Figure 6:
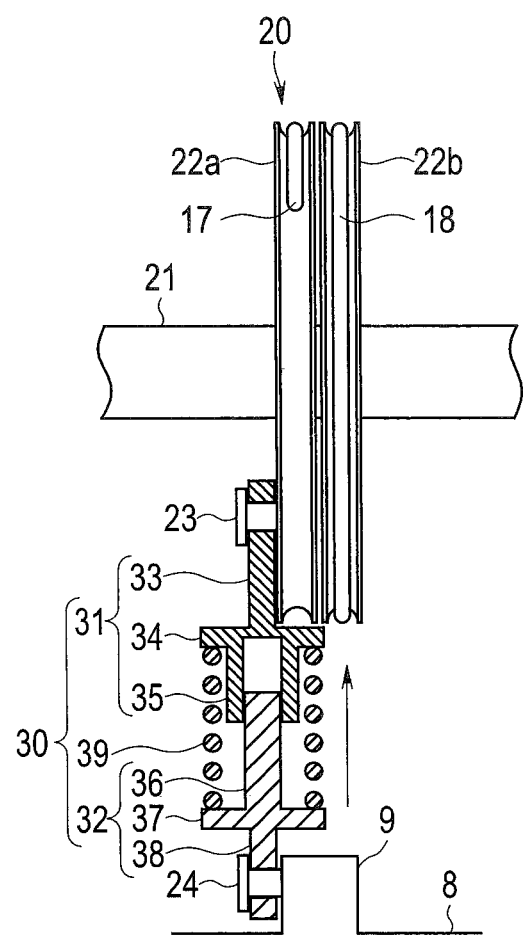
FIG. 6 is a partial cross-sectional view illustrating the action of the amount-of-operation-force reducing portion in the state that the bending portion is bent to the upper part side according to the first embodiment of the present invention.
Figure 7:
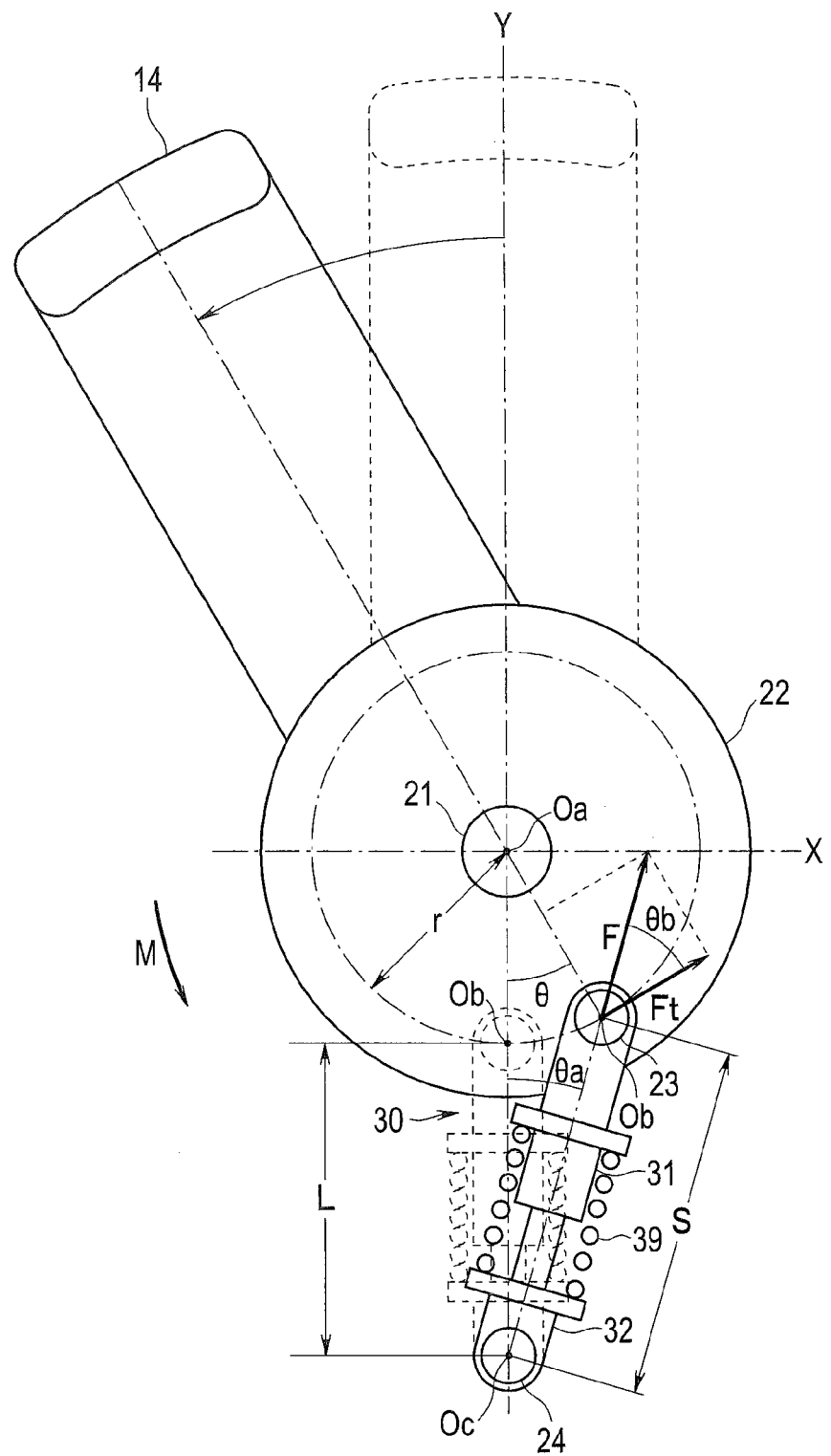
FIG. 7 is a diagram for illustrating a principle of reducing an amount of bending operation force according to the first embodiment of the present invention.
Figure 8:
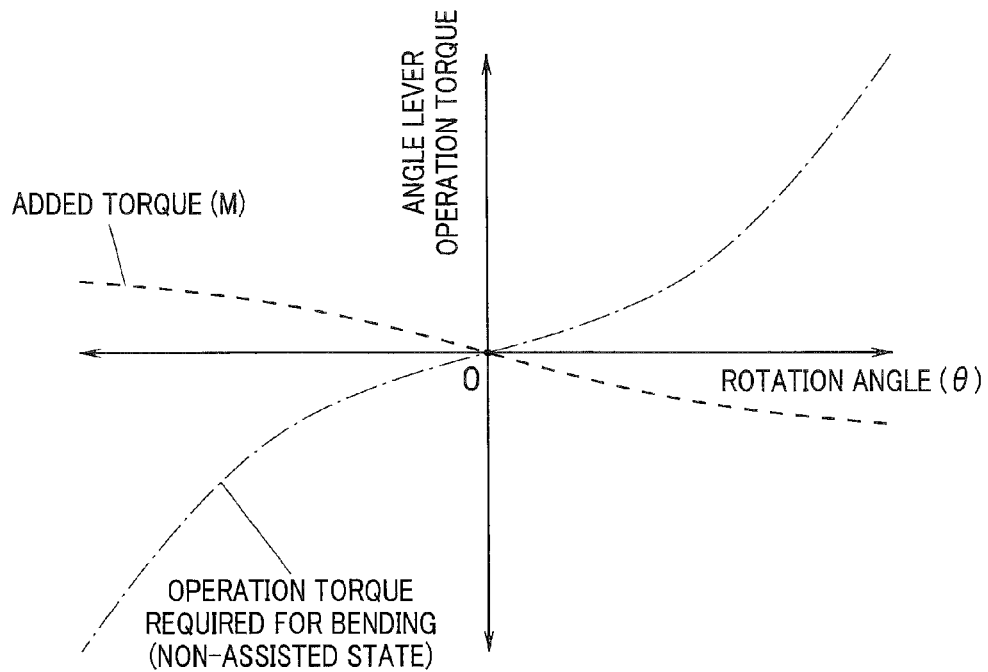
FIG. 8 is a curve graph showing relationships among operation torque of an angle lever, rotation torque and a rotation angle according to the first embodiment of the present invention.
Figure 9:
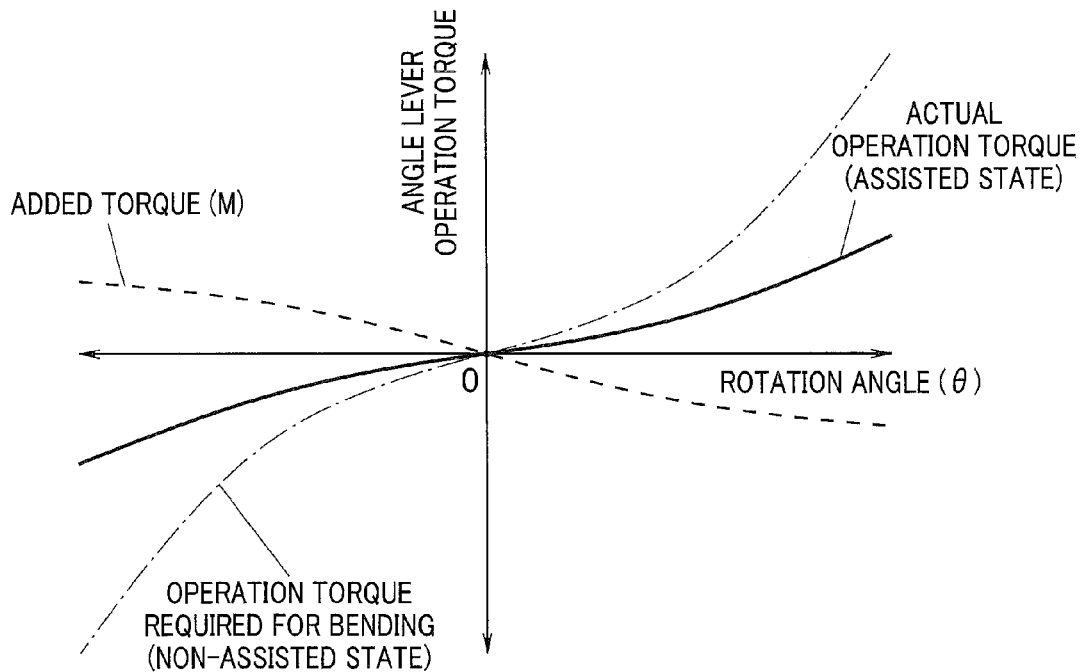
FIG. 9 is a curve graph showing a relationship between actual operation torque obtained by offsetting the operation torque of the angle lever with the rotation torque and the rotation angle, according to the first embodiment of the present invention.
Figure 10:
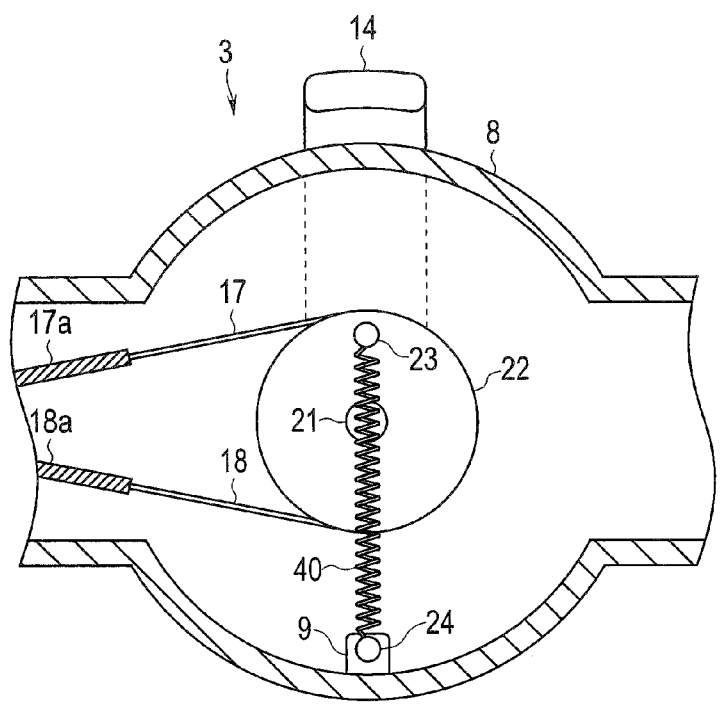
FIG. 10 is a cross-sectional view showing an internal configuration of an operation portion in which the pulley unit is provided with a tension spring, according to a modification according to the first embodiment of the present invention.
Figure 11:
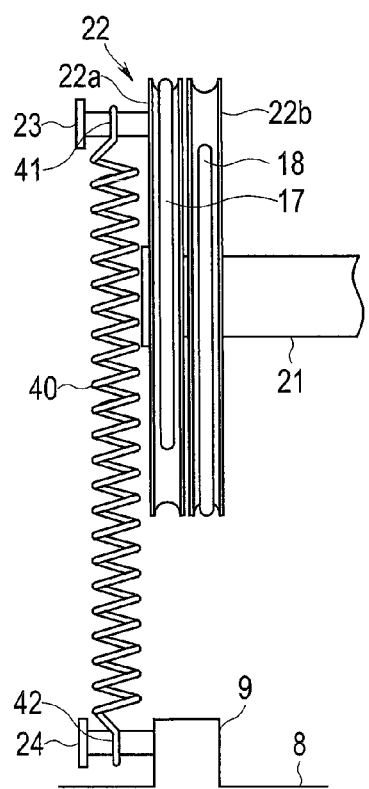
FIG. 11 is a side view showing the configuration in which the pulley unit provided in the operation portion is provided with the tension spring, according to the modification according to the first embodiment of the present invention.
Figure 12:
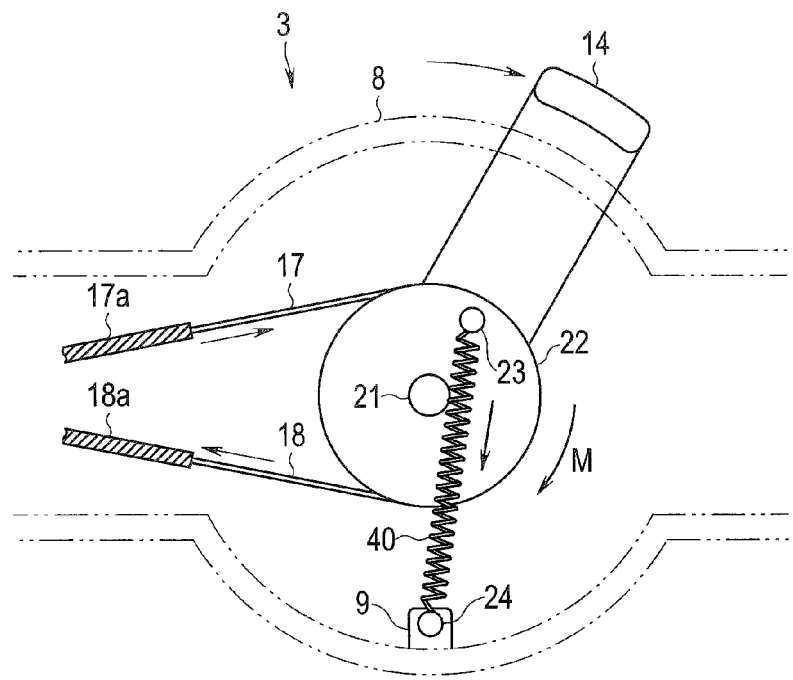
FIG. 12 is a diagram illustrating action of the tension spring in the state that the bending portion is bent to the upper part side, according to the modification according to the first embodiment of the present invention.
Figure 13:
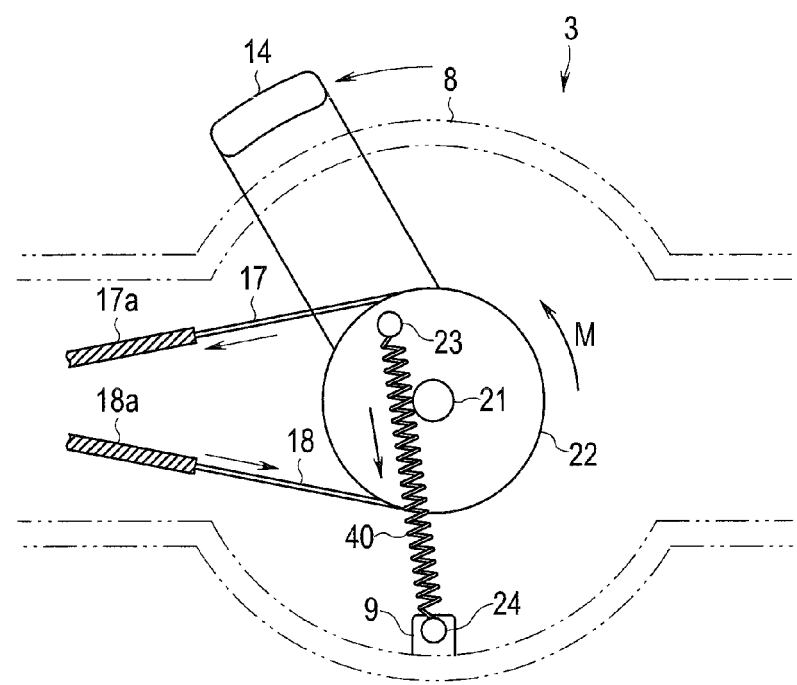
FIG. 13 is a diagram illustrating action of the tension spring in the state that the bending portion is bent to the lower part side, according to the modification according to the first embodiment of the present invention.

FIGS. 1 to 13 relate to the first embodiment of the present invention. FIG. 1 is a perspective view showing a general configuration of an endoscope; FIG. 2 is a cross-sectional view showing an internal configuration of an operation portion; FIG. 3 is a partial cross-sectional view showing a configuration of a pulley unit and an amount-of-operation-force reducing portion which are provided in the operation portion; FIG. 4 is a diagram illustrating action of the amount-of-operation-force reducing portion in a state that a bending portion is bent to an upper part side; FIG. 5 is a diagram illustrating action of the amount-of-operation-force reducing portion in a state that a bending portion is bent to a lower part side; FIG. 6 is a partial cross-sectional view illustrating the action of the amount-of-operation-force reducing portion in the state that the bending portion is bent to the upper part side; FIG. 7 is a diagram for illustrating a principle of reducing an amount of bending operation force; FIG. 8 is a curve graph showing relationships among operation torque of an angle lever, rotation torque and a rotation angle; FIG. 9 is a curve graph showing a relationship between actual operation torque obtained by offsetting the operation torque of the angle lever with the rotation torque and the rotation angle; FIG. 10 is a cross-sectional view showing an internal configuration of an operation portion in which the pulley unit is provided with a tension spring, according to a modification; FIG. 11 is a side view showing the configuration in which the pulley unit provided in the operation portion is provided with the tension spring, according to the modification; FIG. 12 is a diagram illustrating action of the tension spring in the state that the bending portion is bent to the upper part side, according to the modification; and FIG. 13 is a diagram illustrating action of the tension spring in the state that the bending portion is bent to the lower part side, according to the modification.

As shown in FIG. 1, an endoscope 1 is mainly configured having an elongated insertion portion 2, an operation portion 3 coupled to a proximal end of the insertion portion 2, a light guide connector 4 connected to a light source apparatus not shown, and a video connector 5 connected to a video system center not shown.

Note that, in the endoscope 1, the operation portion 3 and the light guide connector 4 are connected via a flexible cable 6 as a universal code, and the light guide connector 4 and the video connector 5 are connected via a communication cable 7.

Mainly a distal end portion 11 and a bending portion 12 which are formed by metallic members such as stainless steel members, and a rigid tube 13 which is a metal tube such as a stainless steel tube are coupled to the insertion portion 2 in that order from a distal end side. The insertion portion 2 is a part to be inserted into a body, and cables to be described later and a light guide are included inside the insertion portion 2.

The operation portion 3 is provided with an angle lever 14 as a bending operation member for remotely controlling the bending portion 12, and various switches 16 for operating the light source apparatus (not shown), the video system center (not shown) and the like. The angle lever 14 is, here, bending operation means capable of operating the bending portion 12 of the insertion portion 2 in two directions of upward and downward directions. Note that a configuration is also possible in which two angle levers are provided so as to bend the bending portion 12 in four directions of upward, downward, right and left directions.

The bending portion 12 of the insertion portion 2 is provided with a plurality of bending pieces not shown, and the bending portion 12 is bent by the plurality of bending pieces being rotated by bending operation wires 17 and 18 which are pulled/slackened by the angle lever 14 (see FIGS. 2 and 3). Further, the bending portion 12 is provided with a bending rubber 12a as an outer cover which covers the plurality of bending pieces.

As shown in FIGS. 2 and 3, a pulley unit 22 which is a rotation member fixed to a rotation shaft 21 connected to the angle lever 14 is rotatably provided in a housing 8 of the operation portion 3. In the pulley unit 22, a first pulley 22a and a second pulley 22b are arranged midway of the rotation shaft 21 side by side.

A rear end of the first bending operation wire 17 is fixed to the first pulley 22a. The first bending operation wire 17 is pulled by the first pulley 22a being rotated in a clockwise direction on the sheet surface of FIG. 2. At this time, the bending portion 12 is bent to an upper part (UP) side by the plurality of bending pieces (not shown) being rotated in response to pulling of the first bending operation wire 17.

A rear end of the second bending operation wire 18 is fixed to the second pulley 22b. The second bending operation wire 18 is pulled by the second pulley 22b being rotated in the clockwise direction on the sheet surface of FIG. 2. At this time, the bending portion 12 is bent to a lower part (DOWN) side by the plurality of bending pieces (not shown) being rotated in response to pulling of the second bending operation wire 18.

Note that the first bending operation wire 17 and the second bending operation wire 18 are inserted in coil pipes 17a and 18a, respectively, in the rigid tube 13 of the insertion portion 2 from the distal end side of the operation portion 3.

Further, the operation portion 3 is provided with an amount-of-operation-force reducing portion 30 as bending operation assisting means for reducing an amount of operation force by the angle lever 14. The amount-of-operation-force reducing portion 30 is rotatably provided between the pulley unit 22 and the housing 8 of the operation portion 3.

More specifically, the amount-of-operation-force reducing portion 30 has a cylinder portion 31, a rod portion 32, and compression springs 39 which are elastic members provided between the cylinder portion 31 and the rod portion 32 as shown in FIG. 3.

The cylinder portion 31 has a connection portion 33, an outward flange 34 and a tube portion 35. Here, the connection portion 33 of the cylinder portion 31 is rotatably supported by a shaft body 23 fixed to an edge part of one face of the first pulley 22a of the pulley unit 22.

The rod portion 32 has a rod 36, an outward flange 37 and a connection portion 38. The connection portion 38 of the rod portion 32 is rotatably supported by a shaft body 24 fixed to a protrusion portion 9 provided on the housing 8 of the operation portion 3. The rod 36 of the rod portion 32 is inserted in the tube portion 35 of the cylinder portion 31, and the compression springs 39 are arranged between the respective outward flanges 34 and 37 so as to surround the tube portion 35 and the rod 36.

In the amount-of-operation-force reducing portion 30, the cylinder portion 31 and the rod portion 32 can freely advance or retreat so as to be guided to go straight, by insertion of the rod 36 into the tube portion 32, and are urged by the compression springs 39 in directions in which they are mutually separated.

Note that, when the bending portion 12 is in a state of a neutral position (neutral) in which the bending portion 12 is straight without being bent, the rotation shaft 21 of the pulley unit 22, the shaft body 23 on a pulley unit 22 side and the shaft body 24 on a housing 8 side are sequentially arranged on a straight line side by side. That is, in the state of the neutral position (neutral) in which the bending portion 12 is straight without being bent, the shaft body 23 is arranged between the rotation shaft 21 and the shaft body 24.

As described above, here, arrangement of each of the rotation shaft 21 of the pulley unit 22, the shaft body 23 on the pulley unit 22 side and the shaft body 24 on the housing 8 side is set so that they are in line with one another when the bending portion 12 is in the straight-line state without being bent.

Note that the rotation shaft 21 of the pulley unit 22, the shaft body 23 on the pulley unit 22 side and the shaft body 24 on the housing 8 side may be arranged at any positions if they are arranged so as to be in line with one another when the bending portion 12 is at the neutral position (neutral) of not being bending-operated. Here, as an example, such a configuration is made that the rotation shaft 21 and the respective shaft bodies 23 and 24 are arranged so as to be in line with one another in an upward-downward direction orthogonal to a left/right direction on the sheet surface of FIG. 2, which is a front/rear direction of the endoscope 1.

In the endoscope 1 of the present embodiment configured as described above, the amount of operation force of the angle lever 14 is reduced by the amount-of-operation-force reducing portion 30 provided in the operation portion 3 at time of operating the angle lever 14 to perform a bending operation of the bending portion 12.

More specifically, as shown in FIG. 4, at time of bending the bending portion 12 to the upper part side by inclining the angle lever 14 to a proximal end side, which is a hand side, the pulley unit 22 rotates in one direction around the rotation shaft 21, the clockwise direction on the sheet surface of FIG. 4, in conjunction with the angle lever 14. Then, accompanying the rotation of the pulley unit 22, the amount-of-operation-force reducing portion 30 is inclined to a distal end side of the endoscope 1.

That is, in the amount-of-operation-force reducing portion 30, the cylinder portion 31 rotates around the shaft body 23 on the pulley unit 22 side, and the rod portion 32 rotates around the shaft body 24 on the housing 8 side. At this time, in the amount-of-operation-force reducing portion 30, the cylinder portion 31 which has received urging force of the compression springs 39 is urged into a direction of being separated from the rod portion 32 (as a reference, a state of FIG. 3 transitions to a state of FIG. 6).

On the other hand, as shown in FIG. 5, at time of bending the bending portion 12 to the lower part side by inclining the angle lever 14 to the distal end side, the pulley unit 22 rotates in one direction around the rotation shaft 21, the counterclockwise direction on the sheet surface of FIG. 5, in conjunction with the angle lever 14. Here, accompanying the rotation of the pulley unit 22, the amount-of-operation-force reducing portion 30 is inclined to a proximal end side of the endoscope 1, and the cylinder portion 31 which has received the urging force of the compression springs 39 of the amount-of-operation-force reducing portion 30 is urged into the direction of being separated from the rod portion 32 (the state of FIG. 3 transitions to the state of FIG. 6).

In this way, the urging force is given from the amount-of-operation-force reducing portion 30 in a direction in which the pulley unit 22 rotates, the pulley unit 22 rotating in conjunction with the angle lever 14 which performs a bending operation of the bending portion 12. That is, at the time of performing a bending operation of the bending portion 12 by the angle lever 14, the amount-of-operation-force reducing portion 30 gives predetermined rotation torque (added torque) to the pulley unit 22 to reduce the amount of operation force of the angle lever 14.

Note that, since the rotation shaft 21 of the pulley unit 22, the shaft body 23 on the pulley unit 22 side and the shaft body 24 on the housing 8 side are located in line with one another when the bending portion 12 is at the neutral position (neutral) of not being bending-operated, the predetermined rotation torque from the amount-of-operation-force reducing portion 30 to the pulley unit 22 is not given.

In other words, the compression springs 39 of the amount-of-operation-force reducing portion 30 are arranged so as to urge force in a direction to a rotation center of the rotation shaft 21 so that rotation torque is not given to the pulley unit 22 when the bending portion 12 is in the neutral-position state in which the bending portion 12 is straight without being bent.

Here, description will be made on the principle of, at the time of performing a bending operation of the bending portion 12 by the angle lever 14, giving rotation torque from the amount-of-operation-force reducing portion 30 to the pulley unit 22 to reduce the amount of operation force of the angle lever 14, based on FIGS. 7 to 9.

Note that, though, for example, the action of reducing the amount of operation force of the angle lever 14 when the angle lever 14 is inclined to the distal end side at the time of performing a bending operation of the bending portion 12 is shown as an example, as shown in FIG. 7, the action of reducing the amount of operation force of the angle lever 14 similarly occurs when the angle lever 14 is inclined to the proximal end side also.

First, rotation torque M given to the pulley unit 22 by the amount-of-operation-force reducing portion 30 can be determined by a following equation (1) which indicates a product of a length (a radius of rotation) r, which is a distance from a center Oa of the rotation shaft 21 to a center Ob of the shaft body 23 on the pulley unit 22 side, and a rotation component Ft, which is tangential force at the center Ob of the shaft body 23 corresponding to urging force F by the compression springs 39 provided for the amount-of-operation-force reducing portion 30.

$$M = r \times Ft \quad \text{Equation (1)}$$

More specifically, first, a distance of separation between the center Ob of the shaft body 23 on the pulley unit 22 side and a center Oc of the shaft body 24 on the housing 8 side at the time when the angle lever 14 is not operated and the bending portion 12 is at the neutral position (neutral) of not being bending-operated is set as a length L.

Then, a distance of separation between the center Ob of the shaft body 23 on the pulley unit 22 side and the center Oc of the shaft body 24 on the housing 8 side at time when the angle lever 14 is inclined and the pulley unit 22 is rotation-operated around the rotation shaft 21 at a predetermined rotation angle θ is set as a length S.

An angle at which the amount-of-operation-force reducing portion 30 rotates around the center Oc of the shaft body 24 on the housing 8 side at time when the pulley unit 22 rotates at the predetermined rotation angle θ is set as a rotation angle θa.

The rotation angle θa can be calculated by a following equation (2) with use of the above lengths r and L and the rotation angle θ.

$$\theta a = A \text{ TAN}(r \times \text{SIN } \theta / L) \quad \text{Equation (2)}$$

Further, the urging force F by the compression springs 39 of the amount-of-operation-force reducing portion 30 at the time when the pulley unit 22 is operated at the predetermined rotation angle θ can be calculated by a following equation (3) with use of a spring constant K of the compression springs 39, the above lengths L and S, and an amount of force Fn of the compression springs 39 at a time when the distance is the length L.

$$F = Fn - K(S - L) \quad \text{Equation (3)}$$

At this time, the rotation component Ft is given to the pulley unit 22 in a tangential direction of a circle passing the center Ob of the shaft body 23. The rotation component Ft is rotation force added to the pulley unit 22 in a direction along a tangential line having a predetermined angle θb relative to the urging force F.

The rotation component Ft can be calculated by a following equation (4) with use of the urging force F and the predetermined angle θb.

$$Ft = F \times \cos \theta b \quad \text{Equation (4)}$$

Note that the predetermined angle θb can be calculated by a following equation (5) with use of the rotation angles θ and θa.

$$\theta b = 90° - (\theta + \theta a) \quad \text{Equation (5)}$$

As described above, the pulley unit 22 is given the rotation component Ft from the amount-of-operation-force reducing portion 30 in a rotation direction having the predetermined angle θb relative to the urging force F of the compression springs 39 of the amount-of-operation-force reducing portion 30 along the tangential line of the circle passing the center Ob of the shaft body 23. Therefore, the rotation torque M calculated by the above equation (1) is given to the pulley unit 22 by the rotation component Ft.

By the way, operation torque required at the time of operating the angle lever 14 for causing the bending portion 12 to bend when the amount-of-operation-force reducing portion 30 is not provided draws a curve indicated by a long-dashed and short-dashed line in FIG. 8, and increases as an absolute value of the rotation angle θ increases. That is, because restoration force of the bending rubber 12a of the bending portion 12 and an amount of force for elastically transforming the bending portion 12 increase accompanying increase in a bending angle of the bending portion 12, the operation torque increases as the absolute value of the rotation angle θ of the pulley unit 22 which changes in conjunction with displacement of the angle lever 14 operated increases.

In comparison, the rotation torque M added from the amount-of-operation-force reducing portion 30 at the time of operating the angle lever 14 draws a curve indicated by a dotted line in FIG. 8, increases as the absolute value of the rotation angle θ increases, and offsets and reduces the operation torque required at the time of operating the angle lever 14. That is, the rotation torque M added from the amount-of-operation-force reducing portion 30 is calculated from a product of the length (the radius of rotation) r which is unchangeable and the rotation component Ft which changes according to the rotation angle θ {the above equation (1)}.

The rotation component Ft which changes according to the rotation angle θ is calculated from a product of the urging force F and a cosine function (cos θb) {the above equation (4)}. The rotation component Ft increases as the absolute value of the rotation angle θ increases because the value of the angle θb decreases as the absolute value of the rotation angle θ increases.

Therefore, the rotation torque M increases as the absolute value of the rotation angle θ increases because the rotation component Ft increases as the rotation angle θ increases. That is, the rotation torque M increases as the absolute value of the rotation angle θ of the pulley unit 22 increases in conjunction with displacement of the angle lever 14 operated, and offsets and reduces the operation torque (the amount of operation force) required at the time of operating the angle lever 14 by an amount of force of the rotation torque M.

In other words, as the rotation angle θ of the pulley unit 22 increases in proportion to an amount of displacement of the angle lever 14 operated and the absolute value of the rotation angle θ increases, the rotation torque M increases.

As described above, the amount of force of the rotation torque M which offsets the operation torque (the amount of operation force) required at the time of operating the angle lever 14 increases in proportion to the amount of displacement of the angle lever 14 and reduces the amount of operation force of the angle lever 14.

In this way, the predetermined rotation torque M is added to the pulley unit 22, according to the rotation angle θ of the pulley unit 22 which rotates according to an operation angle of the angle lever 14 at the time of causing the bending portion 12 to bend, and the amount of operation force of the angle lever 14 decreases such that a curve indicated by a solid line in FIG. 9 is drawn.

Note that an operation range of the angle lever 14 in the present embodiment is a range within which the bending portion 12 is operated at a set maximum bending angle, and the rotation angle θ around the rotation shaft 21 of the pulley unit 22 is between 0° at the neutral position (neutral) at which the bending portion 12 is not bending-operated and ±90°, including 0° and excluding ±90°.

As described above, at the time of performing a bending operation of the bending portion 12, the endoscope 1 of the present embodiment causes the rotation component Ft to be generated from the urging force F of the compression springs 39 of the amount-of-operation-force reducing portion 30, and gives the rotation torque M in the rotation direction of the pulley unit 22 which rotates in response to an inclination operation of the angle lever 14. Thereby, by offsetting the operation torque required at the time of operating the angle lever 14 by the amount of force of the rotation torque M from the amount-of-operation-force reducing portion 30, the endoscope 1 can cause the amount of operation force of the angle lever 14 to be reduced.

As a result, increase in the amount of operation force of the angle lever 14 according to a bending angle, due to the restoring force for returning the bending portion 12 to a straight state by the bending rubber 12a which covers the bending portion 12, the amount of force for elastically deforming the bending rubber 12a, and the like, is reduced, and the endoscope 1 can prevent a user from being tired. Furthermore, the endoscope 1 also has an advantage that, since the force for performing a bending operation of the bending portion 12 by the angle lever 14 is reduced and relieved, bending operability is improved, and it becomes easier to perform a slight operation.

From the above description, the endoscope 1 of the present embodiment reduces the amount of operation force of the angle lever 14, which is an operation member for performing a bending operation of the bending portion 12, prevents a user from being tired, and makes it possible to perform a slight bending operation.

(Modification)

Note that, in the endoscope 1, a tension spring 40, which is an elastic member here, may be used instead of the amount-of-operation-force reducing portion 30 as shown in FIGS. 10 and 12, as a configuration for reducing the amount of operation force of the angle lever 14, which is an operation member for performing a bending operation of the bending portion 12.

More specifically, in the present modification, the arrangement of the shaft body 23 on the pulley unit 22 side is changed, and, when the bending portion 12 is in the state of the neutral position (neutral) in which the bending portion 12 is straight without being bent, the shaft body 23 on the pulley unit 22 side, the rotation shaft 21 of the pulley unit 22 and the shaft body 24 on the housing 8 side are arranged on a straight line side by side.

That is, in the state of the neutral position (neutral) in which the bending portion 12 is straight without being bent, the rotation shaft 21 is arranged between the shaft body 23 and the shaft body 24.

Further, the rotation shaft 21 here is configured so as to rotatably support the pulley unit 22 as a cantilever so as not to come into contact with the tension spring 40.

A hook portion 41 on one end of the tension spring 40 is hooked to the shaft body 23 on the pulley unit 22 side, and a hook portion 42 on the other end is hooked to the shaft body 24 on the housing 8 side.

In the endoscope 1 of the present modification configured as described above, the amount of operation force of the angle lever 14 is reduced by the tension spring 40 provided in the operation portion 3 at the time of performing a rotation operation of the angle lever 14 to perform a bending operation of the bending portion 12.

More specifically, as shown in FIG. 12, at the time of bending the bending portion 12 to the upper part side by inclining the angle lever 14 to the proximal end side, which is the hand side, the pulley unit 22 rotates in one direction around the rotation shaft 21, the clockwise direction on the sheet surface of FIG. 12, in conjunction with the angle lever 14. Accompanying the rotation of the pulley unit 22, the shaft body 23 on the pulley unit 22 side is pulled in a direction in which the tension spring 40 contracts, and a predetermined rotation torque (added torque) is given to the pulley unit 22.

On the other hand, as shown in FIG. 13, at the time of bending the bending portion 12 to the lower part side by inclining the angle lever 14 to the distal end side also, the pulley unit 22 rotates in one direction around the rotation shaft 21, the counterclockwise direction on the sheet surface of FIG. 13, in conjunction with the angle lever 14. Accompanying the rotation of the pulley unit 22, the shaft body 23 on the pulley unit 22 side is pulled in the direction in which the tension spring 40 contracts, and the predetermined rotation torque M is given to the pulley unit 22.

In this way, the shaft body 23 on the pulley unit 22 side is pulled to the tension spring 40 in the direction in which the pulley unit 22, which rotates in conjunction with the angle lever 14 performing a bending operation of the bending portion 12, rotates, and the predetermined rotation torque M is given to the pulley unit 22 at the time of performing a bending operation of the bending portion 12 by the angle lever 14. Thereby, the amount of operation force of the angle lever 14 is reduced.

Note that, since the shaft body 23 on the pulley unit 22 side, the rotation shaft 21 of the pulley unit 22 and the shaft body 24 on the housing 8 side are located in line with one another when the bending portion 12 is at the neutral position (neutral) of not being bending-operated, the predetermined rotation torque to the pulley unit 22 by urging force in the direction in which the tension spring 40 contracts is not given.

That is, here again, the tension spring 40 is arranged so as to urge force in a direction in which the rotation center of the rotation shaft 21 is pulled so that rotation torque is not given to the pulley unit 22 when the bending portion 12 is in the neutral-position state in which the bending portion 12 is straight without being bent.

The configuration of the endoscope 1 described above also has the effect described above and can be a simple configuration in which the tension spring 40 is simply provided. That is, in the endoscope 1 of the present modification, the tension spring 40 constitutes an amount-of-operation-force reducing portion.

(Second Embodiment)

Next, a second embodiment of the present invention will be described.

Note that, in the description below, same reference numerals will be used for common components described in the first embodiment described above, and detailed description of the components will be omitted.

Figure 14:
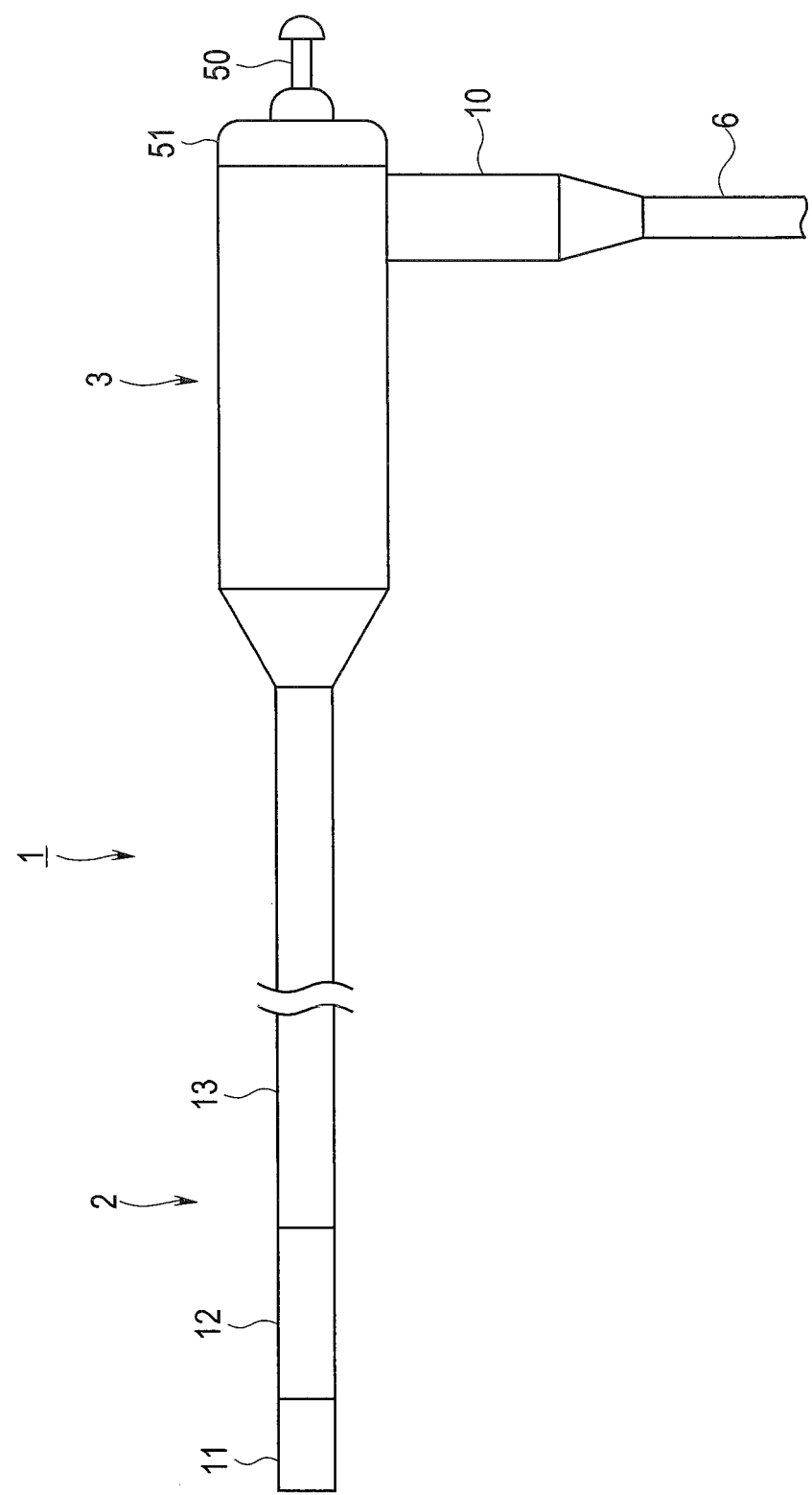
FIG. 14 is a plan view showing a configuration of an endoscope of another aspect according to a second embodiment of the present invention.
Figure 15:
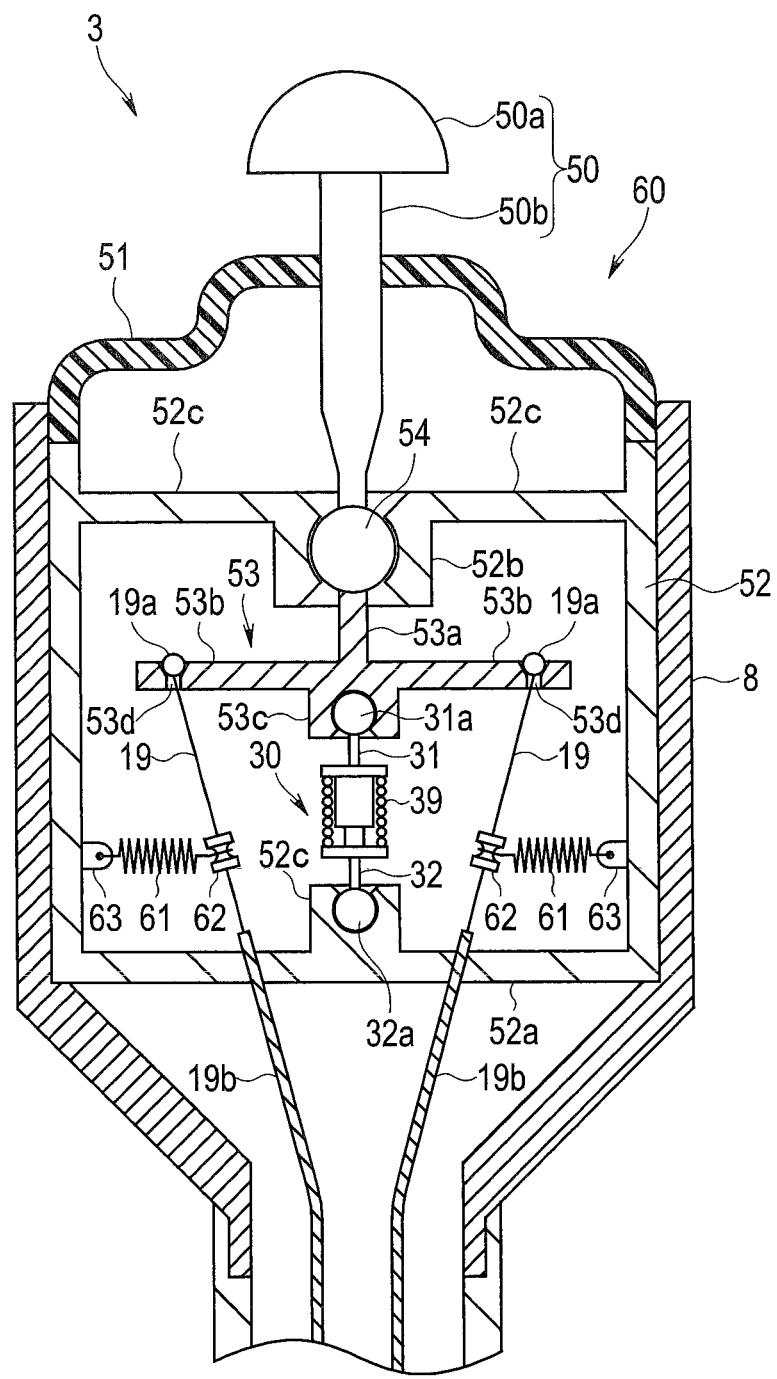
FIG. 15 is a cross-sectional view showing an internal configuration of an operation portion according to the second embodiment of the present invention.
Figure 16:
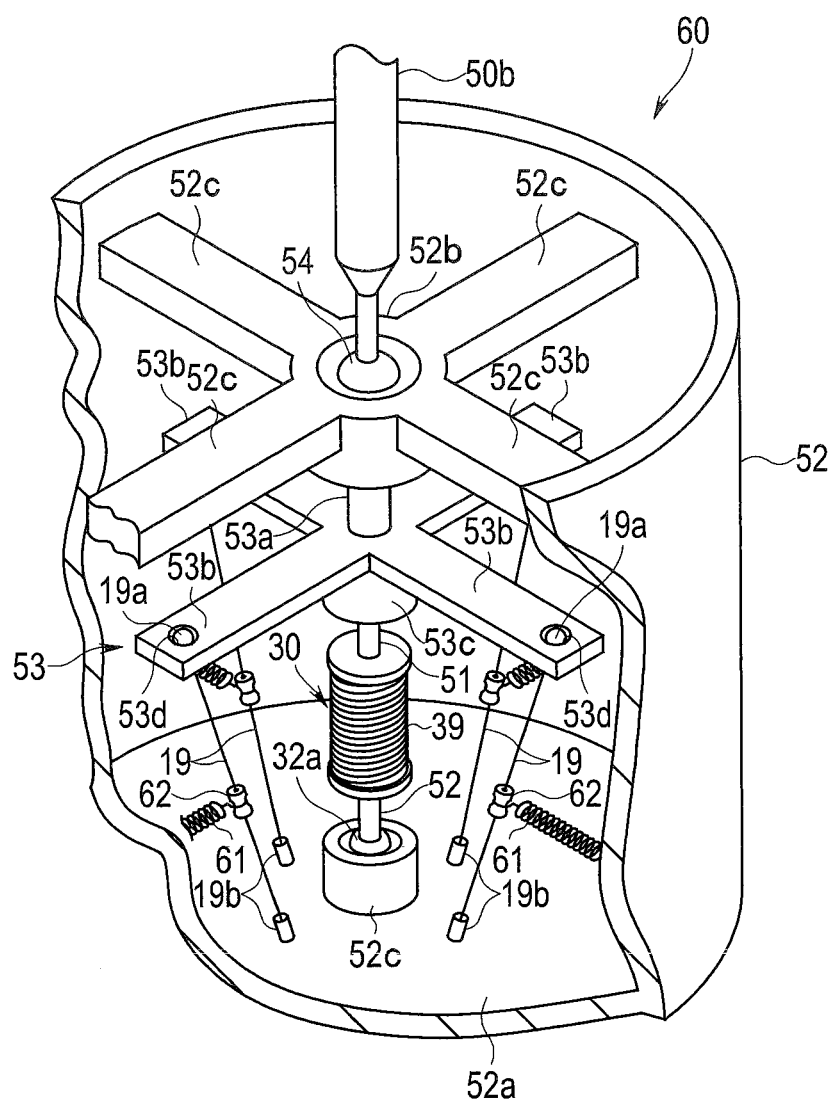
FIG. 16 is a perspective view showing the internal configuration of the operation portion according to the second embodiment of the present invention.
Figure 17:
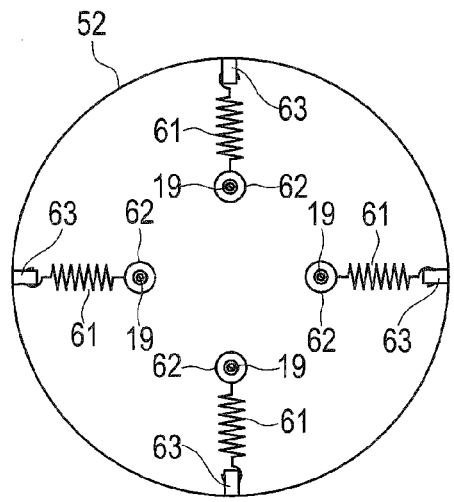
FIG. 17 is a cross-sectional view showing arrangement of tension springs in the operation portion according to the second embodiment of the present invention.
Figure 18:
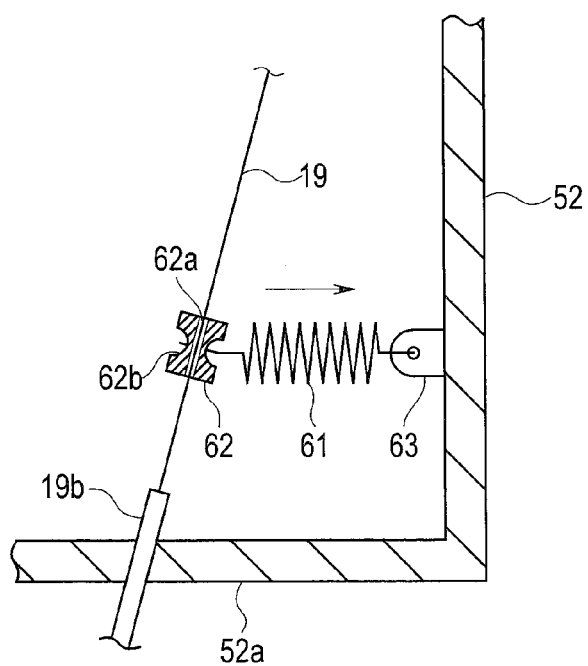
FIG. 18 is a cross-sectional view showing the tension spring, one end of which is hooked to a spring hooking member in which a bending operation wire is inserted and the other end of which is hooked to a projecting portion of a frame portion according to the second embodiment of the present invention.
Figure 19:
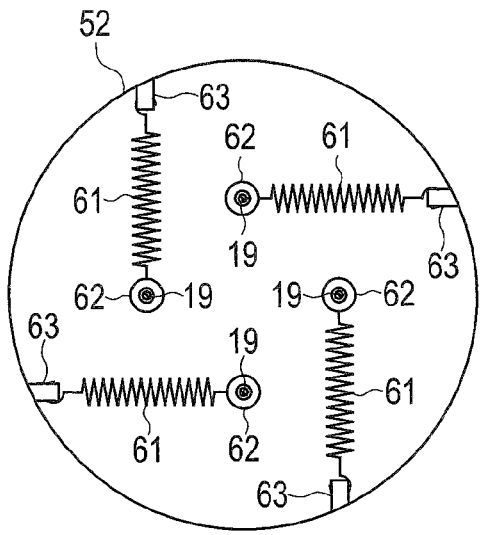
FIG. 19 is a cross-sectional view showing arrangement of the tension springs in the operation portion according to another aspect different from FIG. 17 according to the second embodiment of the present invention.
Figure 20:
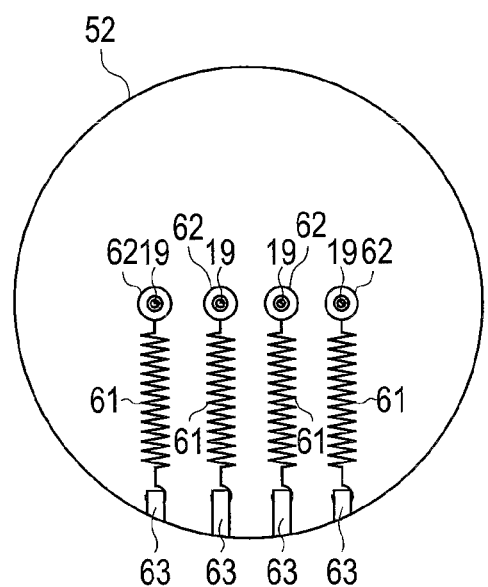
FIG. 20 is a cross-sectional view showing arrangement of the tension springs in the operation portion according to another aspect different from FIGS. 17 and 19 according to the second embodiment of the present invention.
Figure 21:
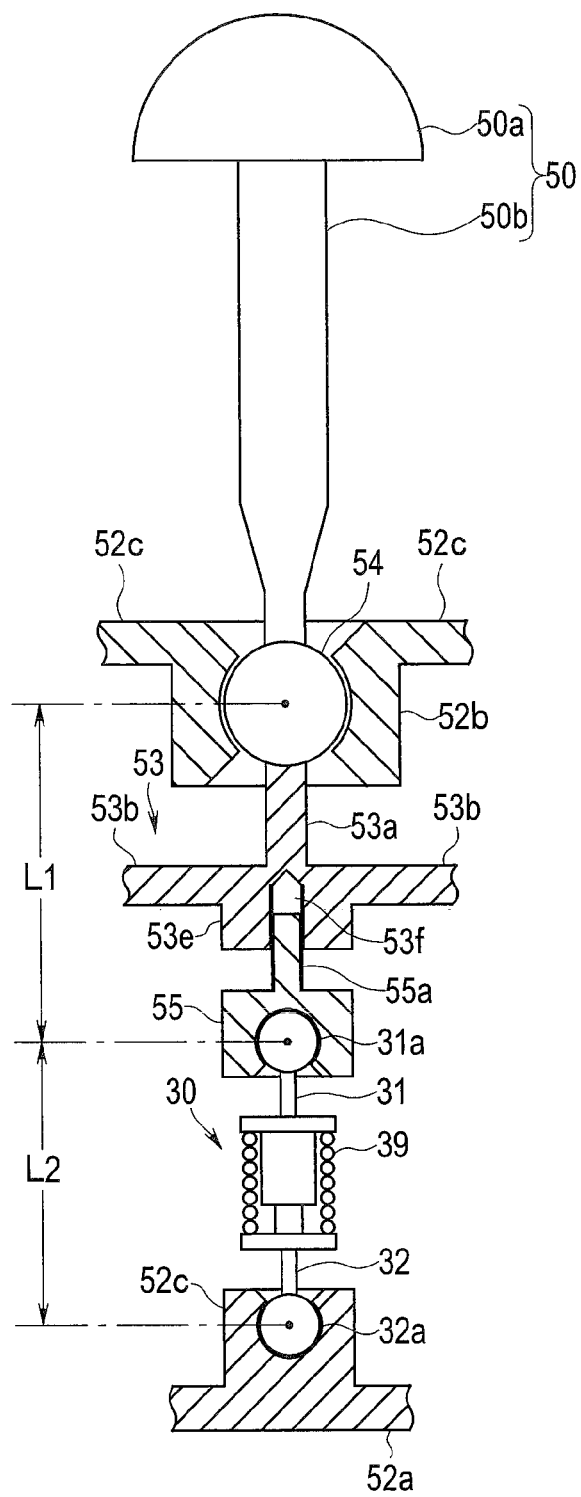
FIG. 21 is a cross-sectional view showing a configuration of a bending operation unit provided in the operation portion according to a first modification according to the second embodiment of the present invention.
Figure 22:
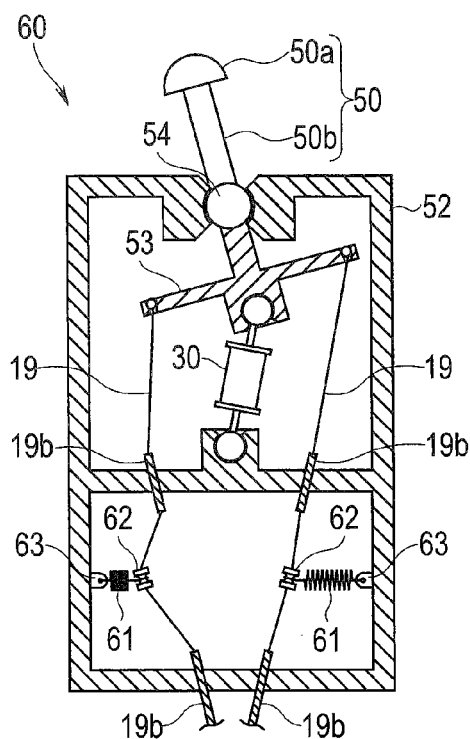
FIG. 22 is a cross-sectional view showing a configuration of the tension springs of the bending operation unit provided in the operation portion according to a second modification according to the second embodiment of the present invention.
Figure 23:
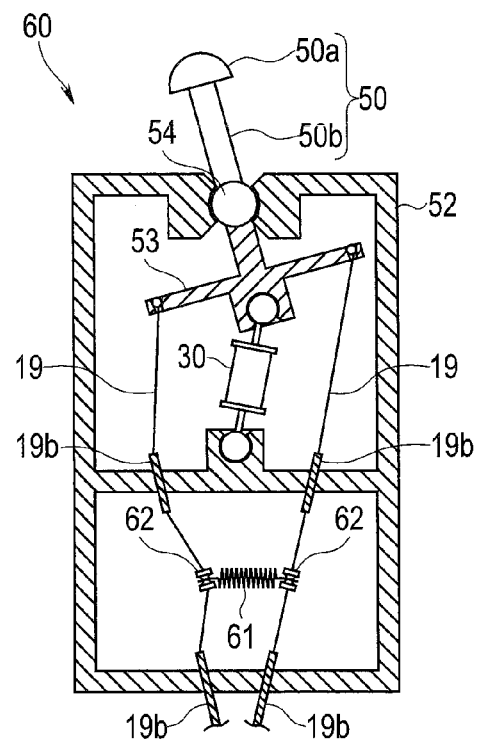
FIG. 23 is a cross-sectional view showing a configuration of the tension springs of the bending operation unit provided in the operation portion according to a third modification according to the second embodiment of the present invention.
Figure 24:
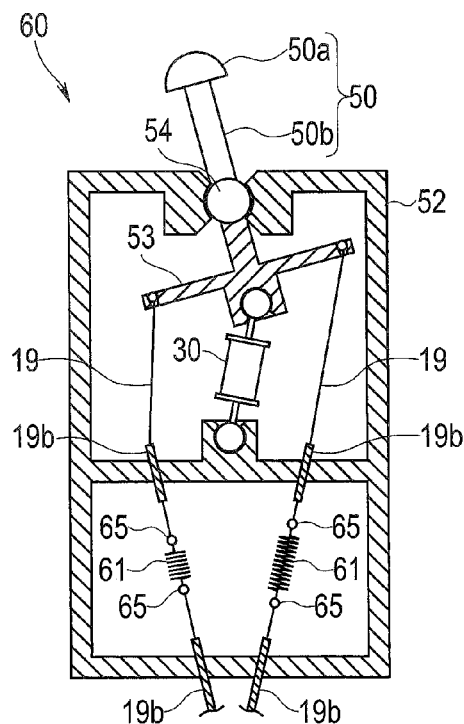
FIG. 24 is a cross-sectional view showing a configuration of the tension springs of the bending operation unit provided in the operation portion according to a fourth modification according to the second embodiment of the present invention.
Figure 25:
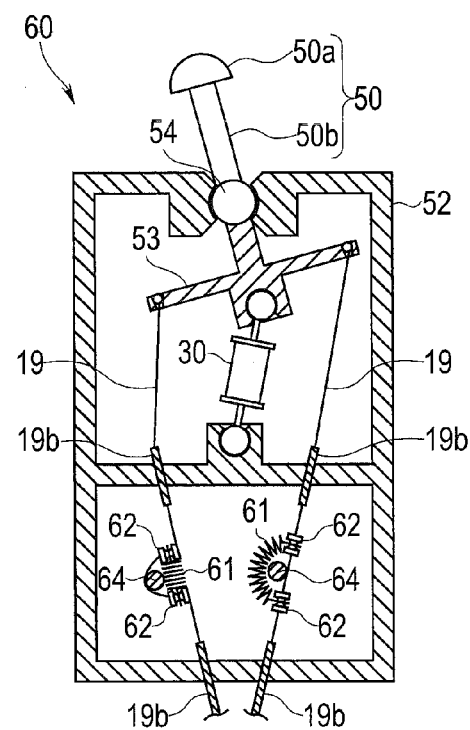
FIG. 25 is a cross-sectional view showing a configuration of the tension springs of the bending operation unit provided in the operation portion according to a fifth modification according to the second embodiment of the present invention.
Figure 26:
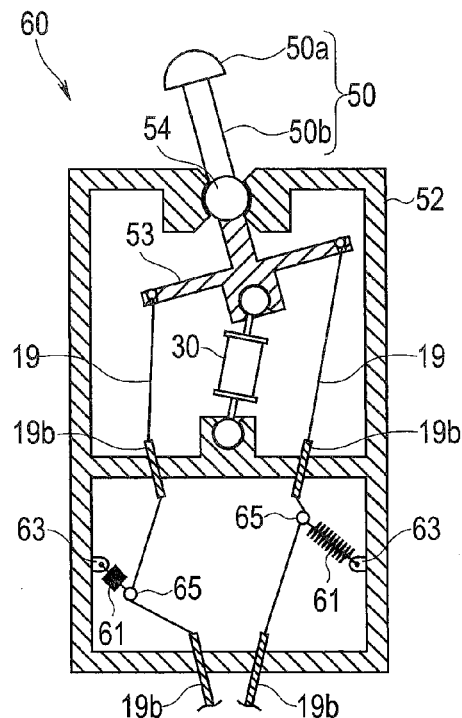
FIG. 26 is a cross-sectional view showing a configuration of the tension springs of the bending operation unit provided in the operation portion according to a sixth modification according to the second embodiment of the present invention.
Figure 27:
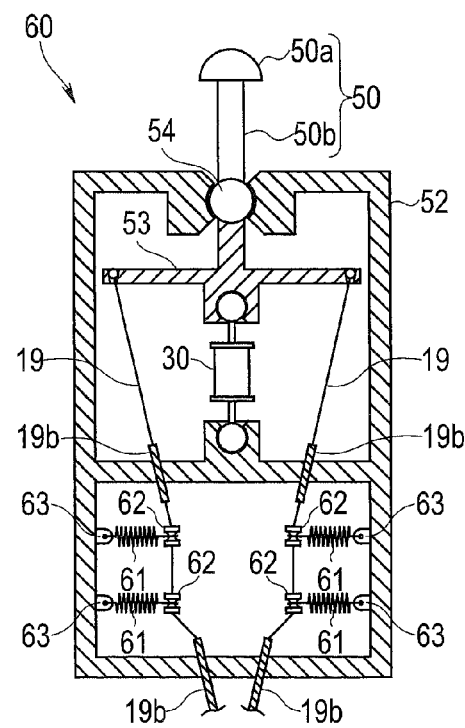
FIG. 27 is a cross-sectional view showing a configuration of the tension springs of the bending operation unit provided in the operation portion according to a seventh modification according to the second embodiment of the present invention.
Figure 28:
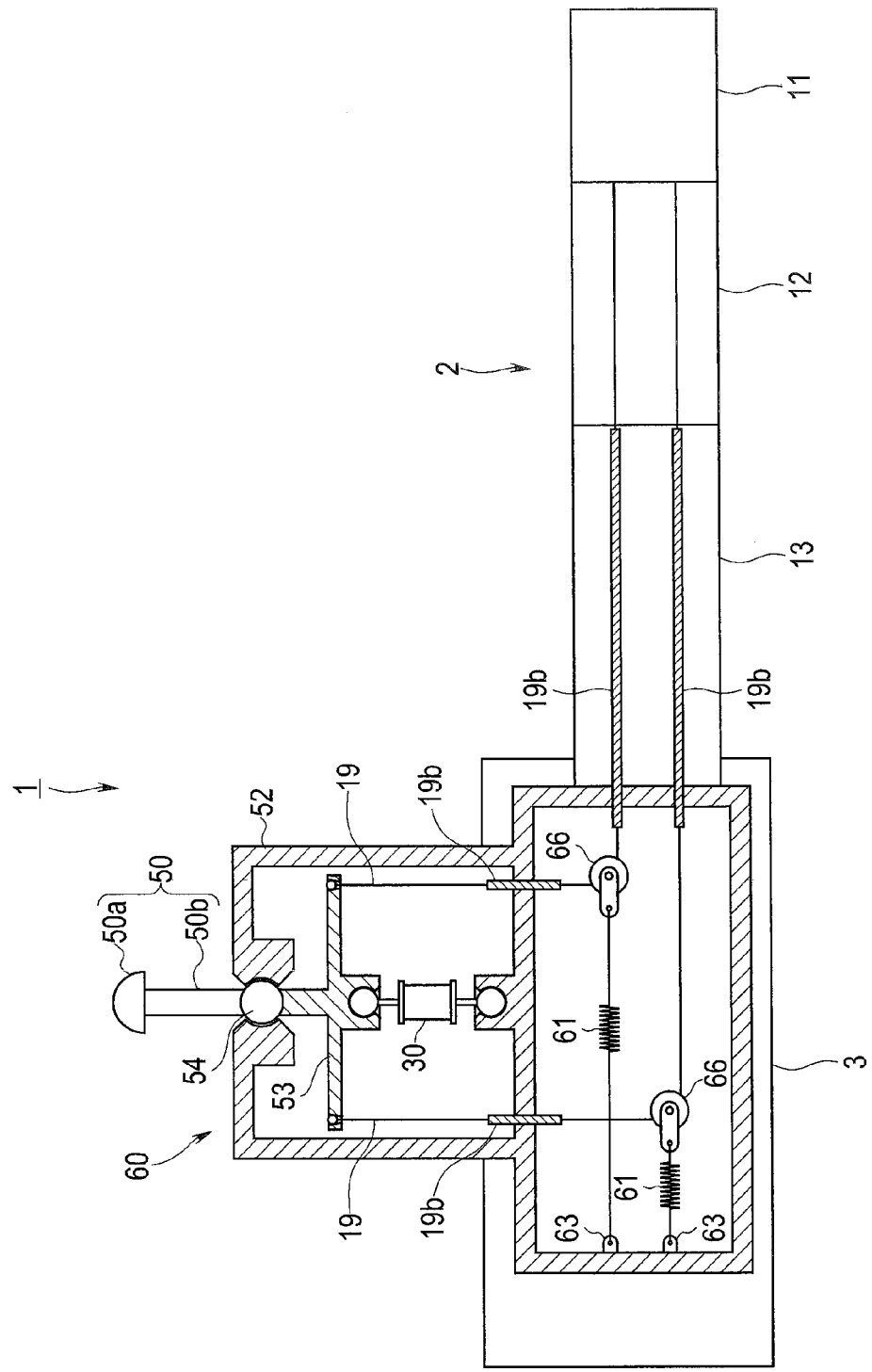
FIG. 28 is a cross-sectional view showing a configuration of the endoscope in which a joystick lever is provided on a side portion of the operation portion, according to an eighth modification according to the second embodiment of the present invention.

Further, FIGS. 14 to 28 relate to the second embodiment of the present invention. FIG. 14 is a plan view showing a configuration of an endoscope; FIG. 15 is a cross-sectional view showing an internal configuration of an operation portion; FIG. 16 is a perspective view showing the internal configuration of the operation portion; FIG. 17 is a cross-sectional view showing arrangement of tension springs in the operation portion; FIG. 18 is a cross-sectional view showing the tension spring, one end of which is hooked to a spring hooking member in which a bending operation wire is inserted, and the other end of which is hooked to a projecting portion of a frame portion; FIG. 19 is a cross-sectional view showing arrangement of the tension springs in the operation portion according to another aspect different from FIG. 17; FIG. 20 is a cross-sectional view showing arrangement of the tension springs in the operation portion according to another aspect different from FIGS. 17 and 19; FIG. 21 is a cross-sectional view showing a configuration of a bending operation unit provided in the operation portion according to a first modification; FIG. 22 is a cross-sectional view showing a configuration of the tension springs of the bending operation unit provided in the operation portion according to a second modification; FIG. 23 is a cross-sectional view showing a configuration of the tension springs of the bending operation unit provided in the operation portion according to a third modification; FIG. 24 is a cross-sectional view showing a configuration of the tension springs of the bending operation unit provided in the operation portion according to a fourth modification; FIG. 25 is a cross-sectional view showing a configuration of the tension springs of the bending operation unit provided in the operation portion according to a fifth modification; FIG. 26 is a cross-sectional view showing a configuration of the tension springs of the bending operation unit provided in the operation portion according to a sixth modification; FIG. 27 is a cross-sectional view showing a configuration of the tension springs of the bending operation unit provided in the operation portion according to a seventh modification; and FIG. 28 is a cross-sectional view showing a configuration of the endoscope in which a joystick lever is provided on a side portion of the operation portion, according to an eighth modification.

As shown in FIG. 14, in an endoscope 1 of the present embodiment, a joystick lever 50 different from the angle lever 14 of the first embodiment is arranged on a proximal end part of the operation portion 3 as a bending operation member for remotely operating the bending portion 12. Further, on a side of the proximal end part of the operation portion 3 here, a grip 10 from which the flexible cable 6 extends is extendedly provided.

Note that the endoscope 1 of the present embodiment is configured so that the bending portion 12 is bendable in the four directions of upward, downward, right and left directions by an inclination operation of the joystick lever 50 provided on the proximal end portion of the operation portion 3.

As shown in FIGS. 15 and 16, the housing 8 of the operation portion 3 is provided with a bending operation unit 60 similarly to the first embodiment. The bending operation unit 60 has mainly the joystick lever 50, a rubber boot 51 which covers the joystick lever 50 in a state that one end portion of the joystick lever 50 projects from the rubber boot 51, a cylinder-shaped frame portion 52, one end of which is blocked and an opening of which at the other end is covered with the rubber boot 51, a wire pulling portion 53 which is movably arranged in the frame portion 52 and which is a rotation member here, and an amount-of-operation-force reducing portion 30 provided between the wire pulling portion 53 and a bottom portion 52a of the frame portion 52 and having a configuration similar to that of the first embodiment.

The joystick lever 50 has a rod 50b, and a hemisphere-shaped finger-putting portion 50a at one end portion of the rod 50b projecting and exposed from the rubber boot 51. The other end of the rod 50b of the joystick lever 50 on the frame portion 52 side is connected to a sphere 54.

On the sphere 54, a bar-shaped connection portion 53a extended from a center of a top of the wire pulling portion 53 is connected on a side opposite to the side where the rod 50b of the joystick lever 50 is connected.

The sphere 54 is movably held by a sphere receiving portion 52b provided in the frame portion 52. That is, the sphere 54 and the sphere receiving portion 52b of the frame portion 52 constitute a so-called boll joint. Thereby, a configuration is made in which, by performing an inclination operation of the joystick lever 50, the wire pulling portion 53 rotates around a center of the sphere 54 and is inclined.

Note that, in the frame portion 52, four holding arm portions 52c are extendedly arranged so as to form a cross shape arranged being extended from an inner circumferential face in an inner diameter direction, and the sphere receiving portion 52b is provided at a center of a crossing of the four holding arm portions 52c. That is, the sphere receiving portion 52b is held at a center of the frame portion 52 by the four holding arm portions 52c.

The wire pulling portion 53 is extendedly arranged with four pulling arm portions 53b are so as to form a cross shape, and a fixation hole 53d for fixing an end portion of a bending operation wire 19 is made near an end of each of the pulling arm portions 53b. By fixation members 19a provided on end portions of the corresponding bending operation wires 19 being inserted in and hooked to the fixation holes 53d, one end of each of the bending operation wires 19 is connected to each of the pulling arm portions 53b.

Note that each bending operation wire 19 is inserted in any of four coil pipes 19b fixed such that one end projects from the bottom portion 52a of the frame portion 52, and is extended to the bending portion 12. Note that, here also, each coil pipe 19b is arranged in the rigid tube 13 of the insertion portion 2. The bending portion 12 is bent to upward, downward, right or left (UP/RL) by the plurality of bending pieces (not shown) provided inside the bending portion 12 rotating according to pulled/slackened states of the four bending operation wires 19.

A sphere receiving portion 53c is provided at a central part of the wire pulling portion 53. The sphere receiving portion 53c movably holds a sphere 31a provided on an end portion of the cylinder portion 31 on an upper part side of the amount-of- operation-force reducing portion 30 on the sheet surface of FIG. 15 (a proximal end side of the endoscope 1). That is, the sphere 31a and the sphere receiving portion 53c constitute a so-called boll joint.

The amount-of-operation-force reducing portion 30 is also provided with a sphere 32a at an end portion of the rod portion 32 on a lower part side on the sheet surface of FIG. 15 (a distal end side of the endoscope 1). The sphere 32a is movably held by the sphere receiving portion 52b provided at a center of the bottom portion 52a of the frame portion 52. That is, the sphere 32a and the sphere receiving portion 52b constitute a so-called boll joint.

By the ball joint configurations, the amount-of-operation-force reducing portion 30 rotates around a center of the sphere 31a of the cylinder portion 31 and a center of the sphere 32a of the rod portion 32 when the wire pulling portion 53 inclines by an operation of the joystick lever 50. The amount-of-operation-force reducing portion 30 is configured so as to be inclined at a predetermined angle in a direction opposite to a direction in which the wire pulling portion 53 is inclined by the operation of the joystick lever 50 then.

In the endoscope 1 of the present embodiment configured as described above, when the wire pulling portion 53 is inclined by an operation of the joystick lever 50, any of the four bending operation wires 19 is pulled or slackened according to inclination of the four pulling arm portions 53b of the wire pulling portion 53. Then, the bending portion 12 is bent in the upward, downward, right or left direction by the plurality of bending pieces (not shown) provided inside the bending portion 12 rotating in a predetermined direction according to pulled/slackened states of the four bending operation wires 19.

At this time, the amount-of-operation-force reducing portion 30 of the present embodiment is inclined at a predetermined angle in a predetermined direction in conjunction with a motion of the wire pulling portion 53, by an operation of the joystick lever 50, and the cylinder portion 31 which has received urging force of the compression springs 39 is urged in a direction against the rod portion 32. That is, the wire pulling portion 53 inclined in conjunction with the operation of the joystick lever 50 for performing a bending operation of the bending portion 12 is given the urging force from the amount-of-operation-force reducing portion 30 in the inclination direction.

Thereby, at the time of performing a bending operation of the bending portion 12 by the joystick lever 50, the amount-of-operation-force reducing portion 30 gives urging force of the compression springs 39 in the direction in which the wire pulling portion 53 is inclined, to reduce the amount of operation force of the joystick lever 50.

In other words, at the time of performing a bending operation of the bending portion 12 by the joystick lever 50, the urging force is added from the amount-of-operation-force reducing portion 30 in the direction in which the wire pulling portion 53 is inclined. At this time, the sphere 54 which is interposed between the joystick lever 50 and the wire pulling portion 53 and is movably held by the sphere receiving portion 52b rotates around its center.

Then, rotation torque occurs around center of the sphere 54 due to the urging force from the amount-of-operation-force reducing portion 30, and the amount of operation force of the joystick lever 50 is reduced.

Since the principle that the amount of operation force of the joystick lever 50 is reduced in this way is similar to that described in the first embodiment with use of FIG. 7, description on the principle will be omitted.

Note that the center of the sphere 54 interposed between the joystick lever 50 and the wire pulling portion 53 corresponds to the center Oa of the rotation shaft 21 of the pulley unit 22; the center of the sphere 31a of the cylinder portion 31 of the amount-of-operation-force reducing portion 30 corresponds to the center Ob of the shaft body 23 on the pulley unit 22 side; and the center of the sphere 32a of the rod portion 32 of the amount-of-operation-force reducing portion 30 corresponds to the center Oc of the shaft body 24 on the housing 8 side.

Therefore, rotation torque around the center of the sphere 54 movably held by the sphere receiving portion 52b, which is given from the amount-of-operation-force reducing portion 30, increases as an absolute value of a rotation angle of the sphere 54 at time when the joystick lever 50 is inclined increases, because a rotation component which occurs around the center of the sphere 54 increases as the absolute value increases.

That is, the rotation torque given from the amount-of-operation-force reducing portion 30 here increases as the absolute value of the rotation angle of the sphere 54 by an operation of the joystick lever 50 increases, and offsets and reduces the operation torque required at time of operating the joystick lever 50 by an amount of force of the rotation torque.

In this way, at the time of bending the bending portion 12, rotation torque is added from the amount-of-operation-force reducing portion 30 according to an operation angle of the joystick lever 50, and the amount of operation force of the joystick lever 50 decreases.

Further, in the present embodiment also, an operation range of the joystick lever 50 is a range within which the bending portion 12 is operated at a set maximum bending angle, and the rotation angle of the sphere 54 is between 0° at the neutral position (neutral) at which the bending portion 12 is not bending-operated and ±90°, including 0° and excluding ±90°.

As described above, in the endoscope 1 of the present embodiment also, it is possible to, at the time of performing a bending operation of the bending portion 12, cause a rotation component from urging force from the compression springs 39 of the amount-of-operation-force reducing portion 30 to give rotation torque to the wire pulling portion 53 in the rotation direction of the sphere 54 which rotates in response to an inclination operation of the joystick lever 50, offset the operation torque required at the time of operating the joystick lever 50 by the amount of force of the rotation torque and reduce the amount of operation force of the joystick lever 50, similarly to the first embodiment.

Thereby, increase in the amount of operation force of the joystick lever 50 according to a bending angle, due to the restoring force for returning the bending portion 12 to a straight state by the bending rubber 12a which covers the bending portion 12, the amount of force for elastically deforming the bending rubber 12a, and the like, is reduced, and the endoscope 1 can prevent a user from being tired. Furthermore, the endoscope 1 also has an advantage that, since the force for performing a bending operation of the bending portion 12 by the joystick lever 50 is reduced and relieved, bending operability is improved, and it becomes easier to perform a slight operation.

From the above description, the endoscope 1 of the present embodiment also reduces the amount of operation force of the joystick lever 50, which is an operation member for performing a bending operation of the bending portion 12, prevents a user from being tired, and makes it possible to perform a slight bending operation.

By the way, in the configuration of performing a bending operation of the bending portion 12 by the joystick lever 50 like the endoscope 1 of the present embodiment, it is possible to perform various bending operations of the bending portion 12 in the upward, downward, right and left directions by rotating the joystick lever 50 in a circumferential direction around a central axis of the operation portion 3 in a state that the joystick lever 50 is inclined.

However, in the endoscope 1, two bending operation wires 19 form a pair of pulling and slackening states according to a bending state of the bending portion 12 because the bending portion 12 is bending-operated by pulling/slackening the four bending operation wires 19; and, especially when a loosened bending operation wire 19 is pulled, the joystick lever 50 falls down swiftly and cannot be smoothly operated.

Therefore, it is not possible to perform a smooth bending operation of the bending portion 12 by the joystick lever 50, and the endoscope 1 gives an uncomfortable feeling to a user at the time of performing a bending operation. Further, if a loosened bending operation wire 19 is pulled suddenly at time of changing a bending direction of the bending portion 12, the bending portion 12 cannot move continuously and smoothly, and it becomes difficult to determine a direction at time of performing photographing aiming at an examination target site and an endoscopic image is instantaneously switched, that is, so-called image jump occurs by the bending portion 12 poppingly moving intermittently.

In order to prevent the phenomena, the endoscope 1 of the present embodiment is configured such that an elastic member is provided as a pulling member for providing a state of being continuously tensioned so that each of the bending operation wires 19 is not loosened.

More specifically, returning to FIGS. 15 and 16, the endoscope 1 here is provided with four tension springs 61 as pulling springs which are elastic members for pulling and tensioning the bending operation wires 19 in an outer diameter direction of the frame portion 52 so that each bending operation wire 19 is in a predetermined direction, for example, in such a manner that the tension springs 61 have a predetermined angle relative to longitudinal directions of the pulled bending operation wires 19, in the frame portion 52 of the bending operation unit 60 provided in the operation portion 3. Note that the elastic members are not limited to the tension springs 61, and rubber may be used.

One end of each tension spring 61 is hooked to a body portion of a spring hooking member 62, and the other end is hooked and fixed to a projecting member 63 having a hole portion and arranged on an inner circumference of the frame portion 52.

Note that, as shown in FIG. 18, the spring hooking member 62 has a hole portion 62a in which the bending operation wire 19 is inserted, and is slidable along the bending operation wire 19. Further, a circumference groove 62b for hooking one end of the tension spring 61 is formed in the body portion of the spring hooking member 62.

As described above, each bending operation wire 19 is in the state of being continuously tensioned by being pulled in the outer diameter direction of the frame portion 52 by the tension spring 61.

Therefore, in the endoscope 1 of the present embodiment, a bending operation wire 19 in a slackened state is not in a state of being loosened according to a bending state of the bending portion 12, and it does not happen that the joystick lever 50 falls down swiftly. Therefore, it becomes possible to operate the joystick lever 50 smoothly, and it does not happen that an uncomfortable feeling is given to a user at the time of performing a bending operation due to operability of the smooth bending operation of the bending portion 12 by the joystick lever 50.

Furthermore, in the endoscope 1, since a bending operation wire 19 in the slackened state is tensioned and is not loosened, the bending portion 12 can bend continuously and smoothly even if the bending operation wire 19 is pulled suddenly at the time of changing the bending direction of the bending portion 12.

As a result, in the endoscope 1 it is easy to determine a direction at the time of performing photographing aiming at an examination target site, and the bending portion 12 can smoothly bend. Therefore, it is possible to prevent an endoscopic image from being instantaneously switched, that is, occurrence of the so-called image jump.

Note that each tension springs 61 is not limited to the arrangement/configuration of pulling each bending operation wire 19 in the outer diameter direction of the frame portion 52 as shown in FIG. 17 in order that each bending operation wire 19 is in the state of being continuously tensioned, but the arrangement/configuration can be freely changed.

For example, positions on the frame portion 52 to which the tension springs 61 are fixed may be changed as shown in FIG. 19 or 20 to change a pulling direction of each bending operation wire 19 by each tension springs 61.

Thereby, insertion routes of the respective bending operation wires 19 can be changed according to an array of the respective tension springs 61, and it becomes easy to perform appropriate design according to arrangement of cables, switches and the like provided for the operation portion 3.

(Modifications)

Note that configurations of various modifications described below may be adopted for the endoscope 1 of the present embodiment.

(First Modification)

The present modification is an example of making it possible to adjust the rotation torque given from the amount-of-operation-force reducing portion 30 according to an operation angle of the joystick lever 50.

As shown in FIG. 21, the wire pulling portion 53 here is provided with a protrusion portion 53e projecting to a lower part side on the sheet surface of FIG. 21 and from which the four pulling arm portions 53b described above are extendedly arranged, at a central part. At a center of the protrusion portion 53e, a female screw hole 53f is formed from the lower part side.

A male screw portion 55a of a sphere receiving portion 55 which movably holds the sphere 31a provided at the end portion of the cylinder portion 31 of the amount-of-operation-force reducing portion 30 is screwed in the female screw hole 53f of the protrusion portion 53e. Note that the male screw portion 55a is provided such that it projects to an upper part side on the sheet surface of FIG. 21 from a center of a surface of the sphere receiving portion 55.

That is, the sphere 31a and the sphere receiving portion 55 constitutes a so-called ball joint, and the amount-of-operation-force reducing portion 30 here is configured so as to rotate around the center of the sphere 31a of the cylinder portion 31.

In the present modification configured as described above, it is possible to change a length L1, which is a distance of separation between the center of the sphere 54 interposed among the joystick lever 50 and the wire pulling portion 53 and the center of the sphere 31a of the cylinder portion 31 of the amount-of-operation-force reducing portion 30, by changing a screwed amount of the male screw portion 55a of the sphere receiving portion 55 screwed into the female screw hole 53f formed in the protrusion portion 53e of the wire pulling portion 53.

Further, in the amount-of-operation-force reducing portion 30, a length L2, which is a distance of separation between the center of the sphere 31a of the cylinder portion 31 and the center of the sphere 32a of the rod portion 32, is changed, accompanying change in the screwed amount of the male screw portion 55a screwed into the female screw hole 53f.

Note that, even if the screwed amount of the male screw portion 55a screwed into the female screw hole 53f is changed, a length (L1+L2), which is a distance of separation between the center of the sphere 54 interposed among the joystick lever 50 and the wire pulling portion 53 and the center of the sphere 32a of the rod portion 32 of the amount-of-operation-force reducing portion 30, is not changed but is constant.

In the endoscope 1 of the present modification configured as described above, it is possible to increase the rotation torque given from the amount-of-operation-force reducing portion 30 according to an operation angle of the joystick lever 50, by extending the length L1, which is the distance of separation between the center of the sphere 54 interposed among the joystick lever 50, the sphere 54 and the wire pulling portion 53 and the center of the sphere 31a of the cylinder portion 31 of the amount-of-operation-force reducing portion 30.

In other words, in the endoscope 1, the urging force of the compression springs 39 increases by shortening the length L2, which is the distance of separation between the center of the sphere 31a of the cylinder portion 31 and the center of the sphere 32a of the rod portion 32 in the amount-of-operation-force reducing portion 30.

As described above, the endoscope 1 of the present modification is adapted to make it possible to adjust the rotation torque given from the amount-of-operation-force reducing portion 30 only by changing the screwed amount of the male screw portion 55a of the sphere receiving portion 55 screwed into the female screw hole 53f formed in the protrusion portion 53e of the wire pulling portion 53, and, thereby, it is possible to optimize the amount of operation force of the joystick lever 50.

(Second Modification)

The present modification is an example of an arrangement of the tension springs 61 for causing the bending operation wires 19 to be in the state of being continuously tensioned without being loosened.

The tension spring 61 may be arranged so that the bending operation wire 19 is pulled to the outer diameter direction of the frame portion 52, between the coil pipes 19b in which the bending operation wire 19 is inserted, as shown in FIG. 22.

(Third Modification)

The present modification is an example about a configuration of the tension spring 61 for causing the bending operation wire 19 to be in the state of being continuously tensioned without being loosened.

Such a configuration is also possible that one tension spring 61 both ends of which are hooked to the spring hooking members 62 is provided so as to connect two paired bending operation wires 19 for performing an upward/downward-direction or right/left-direction bending operation of the bending portion 12 is provided between the coil pipes 19b in which each bending operation wire 19 is inserted, so that the two bending operation wires 19 are in the state of being continuously tensioned without being loosened, as shown in FIG. 23.

(Fourth Modification)

The present modification is also an example about a configuration of the tension spring 61 for causing the bending operation wire 19 to be in the state of being continuously tensioned without being loosened.

Such a configuration is also possible that the tension spring 61 is interposed between the coil pipes 19b in which the bending operation wire 19 is inserted, along a longitudinal direction of the bending operation wire 19 to cause the bending operation wire 19 to be in the state of being continuously tensioned without being loosened, as shown in FIG. 24.

(Fifth Modification)

The present modification is also an example about a configuration of the tension spring 61 for causing the bending operation wire 19 to be in the state of being continuously tensioned without being loosened.

Such a configuration is also possible that, between the coil pipes 19b in which each bending operation wire 19 is inserted, the tension spring 61 is provided such that it becomes slidable relative to the bending operation wire 19 by hooking both ends to the spring hooking members 62, and a cylinder-shaped member 64 is provided being sandwiched between the bending operation wire 19 and the tension spring 61, so that the bending operation wire 19 is caused to be in the state of being continuously tensioned without being loosened, as shown in FIG. 25.

(Sixth Modification)

The present modification is also an example about a configuration of the tension spring 61 for causing the bending operation wire 19 to be in the state of being continuously tensioned without being loosened.

Such a configuration is also possible that, between the coil pipes 19b in which each bending operation wire 19 is inserted, a fixing portion 65 for fixing one end of the tension spring 61 to the bending operation wire 19 is provided without providing the spring hooking members 62 to cause the bending operation wire 19 to be in the state of being continuously tensioned without being loosened, as shown in FIG. 26. Thereby, abrasion between the bending operation wire 19 and the spring hooking members 62 is prevented, and durability is improved.

Note that the present modification is a configuration which is also applicable to the embodiment shown in FIGS. 15 and 16 and the second and third modifications.

(Seventh Modification)

The present modification is also an example about a configuration of the tension spring 61 for causing the bending operation wire 19 to be in the state of being continuously tensioned without being loosened.

Such a configuration is also possible that, between the coil pipes 19b in which each bending operation wire 19 is inserted, two tension springs 61 with weak tensile force are provided to cause the bending operation wire 19 to be in the state of being continuously tensioned without being loosened, as shown in FIG. 27.

Note that, here also, such a configuration is possible that one end of the tension spring 61 is fixed to the bending operation wire 19 without providing the spring hooking members 62, similarly to the sixth modification shown in FIG. 26.

(Eighth Modification)

The present modification is an example about arrangement/configuration of the joystick lever 50 provided on the bending portion 12.

The endoscope 1 may be configured being provided with the joystick lever 50 on one side portion of the operation portion 3 as shown in FIG. 28.

Note that, in the present modification, a pulley unit 66 for changing the direction of each bending operation wire 19 in the operation portion 3 is provided, and the tension springs 61 for pulling the pulley units 66 to a proximal end side of the operation portion 3 are provided so as to cause the bending operation wire 19 to be in the state of being continuously tensioned without being loosened.

REFERENCE EXAMPLE

Figure 29:
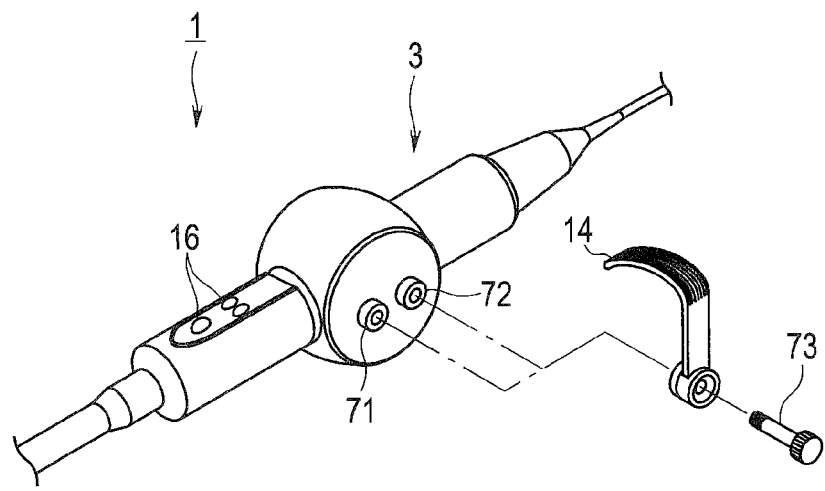
FIG. 29 is an exploded perspective view showing a bending operation lever attachable to and detachable from an operation portion of an endoscope according to a reference example.
Figure 30:
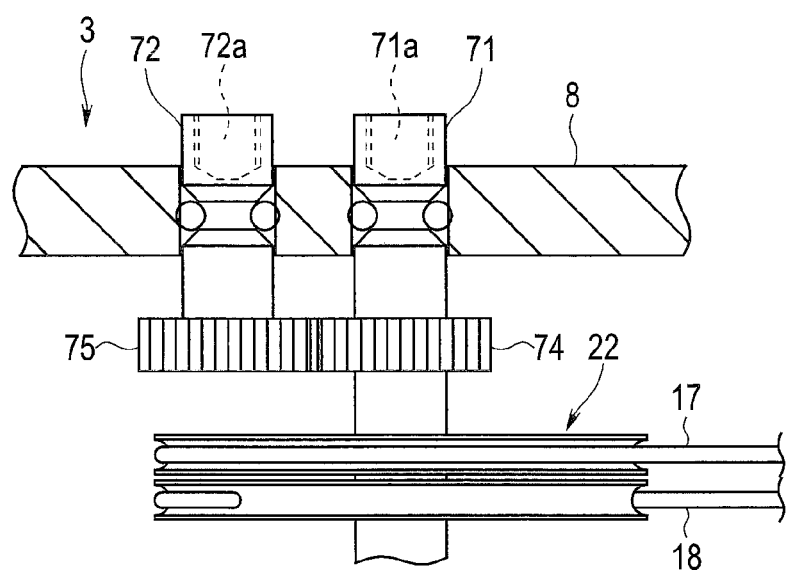
FIG. 30 is a cross-sectional view showing a configuration of two rotation shafts which the bending operation lever is selectively attachable to and detachable from, according to the reference example.

As a reference example of the endoscope 1, such a configuration is also possible that a first rotation shaft 71 and a second rotation shaft 72 are provided on the operation portion 3, and the angle lever 14 is selectively attachable to and detachable from the first and second rotation shafts 71 and 72, as shown in FIGS. 29 and 30.

Note that FIG. 29 is an exploded perspective view showing a bending operation lever attachable to and detachable from an operation portion of an endoscope; and FIG. 30 is a cross-sectional view showing a configuration of two rotation shafts which the bending operation lever is selectively attachable to and detachable from.

Screw holes 71a and 72a for screwing and fixing a fixing screw 73 for fixing the angle lever 14 are formed in the first and second rotation shafts 71 and 72, respectively.

Note that the pulley unit 22 is provided on the first rotation shaft 71, and a flat-toothed gear 74 is interposed between the pulley unit 22 and the housing 8 of the operation portion 3. Further, the second rotation shaft 72 is provided with a flat-toothed gear 75 engaged with the gear 74 of the first rotation shaft 71.

In the endoscope 1 configured as described above, the bending operation direction of the bending portion 12 by the angle lever 14 can be selected by fixing the angle lever 14 to the first rotation shaft 71 or the second rotation shaft 72 selectively.

That is, if the angle lever 14 is attached to the first rotation shaft 71, the pulley unit 22 rotates in a direction corresponding to a rotation direction according to a direction of an operation by the angle lever 14.

On the other hand, if the angle lever 14 is attached to the second rotation shaft 72, the pulley unit 22 rotates in a direction opposite to a rotation direction according to a direction of an operation by the angle lever 14, by the gears 74 and 75.

Thus, in the endoscope 1, the direction of a bending operation of the bending portion 12 by the angle lever 14 is reversed according to whether the first rotation shaft 71 or the second rotation shaft 72 is fitted.

According to above description, the endoscope 1 makes it possible to select the direction of a bending operation of the bending portion 12 by the angle lever 14 according to which the user wishes.

The inventions described in the above embodiments are not limited to the embodiments and the modifications, and, further, it is possible to practice various modifications at an implementation stage within a range not departing from the spirit of the invention. Furthermore, the above embodiments include inventions at various stages, and various inventions can be extracted from appropriate combination of a plurality of disclosed constituent features.

For example, if the stated problem can be solved, and the stated effect can be obtained even if some constituent features are deleted from all constituent features shown in the embodiments, then the configuration from which the constituent features have been deleted can be extracted as an invention.

What is claimed is:

1. An endoscope comprising:
   an insertion portion provided with a bending portion at a distal end part;
   an operation portion coupled to the insertion portion;
   four operation wires insertedly arranged inside the insertion portion and the operation portion, the four operation wires causing the bending portion to bend by being pulled/slackened;
   one operation member provided on the operation portion, the operation member having a rotation portion and being capable of performing a bending operation of the bending portion in four directions by being inclined with the rotation portion as a center;
   a rotation member provided in the operation portion and having a proximal end side and a distal end side, the proximal end side being connected to an opposite side of the operation member with the rotation portion as a center, and the rotation member pulling/slackening the four operation wires by being inclined with the rotation portion as a center in conjunction with an inclination operation of the operation member; and
   an amount-of-operation-force reducing portion, an end portion of which is movably held on the distal end side of the rotation member, the amount-of-operation-force reducing portion applying rotation torque to the rotation member in a direction in which the rotation member is inclined, in response to inclination of the operation member, to reduce an amount of operation force of the operation member, wherein the rotation torque of the amount-of-operation-force reducing portion increases with an increasing displacement of the operation member to offset and reduce the amount of operation force required for the inclination operation of the operation member.

2. The endoscope according to claim 1, wherein, as for the rotation torque, a small rotation torque is applied to the rotation member when an amount of displacement of the operation member operated is small, and a large rotation torque is applied to the rotation member when the amount of displacement is large, to offset and reduce the amount of operation force required for the operation member.

3. The endoscope according to claim 1, wherein the amount-of-operation-force reducing portion is provided with an elastic member for applying the rotation torque to the rotation member in a rotation direction of the rotation member.

4. The endoscope according to claim 3, wherein the elastic member is a compression spring urging the rotation member to apply the rotation torque applied to the rotation member in the rotation direction of the rotation member.

5. The endoscope according to claim 4, wherein the compression spring is arranged so as to urge force toward a rotation center of the rotation member so that the rotation torque is not applied to the rotation member when the bending portion is in a neutral-position state in which the bending portion is straight without being bent.

6. The endoscope according to claim 1, wherein the plurality of operation wires are provided with pulling members providing a state of being tensioned at least when the bending portion is in the neutral-position state in which the bending portion is straight without being bent, even in a state of being slackened.

7. The endoscope according to claim 6, wherein the pulling members pull the plurality of operation wires in a direction having a predetermined angle relative to a longitudinal direction of the plurality of operation wires.

8. The endoscope according to claim 6, wherein the pulling members are slidably connected to the plurality of operation wires.

9. The endoscope according to claim 6, wherein the pulling members are fixedly connected to the plurality of wires.

10. The endoscope according to claim 6, wherein the pulling members are pulling springs pulling the plurality of operation wires.

* * * * *